US010736731B2

(12) United States Patent
Anderson et al.

(10) Patent No.: US 10,736,731 B2
(45) Date of Patent: Aug. 11, 2020

(54) CORNEAL FILLERS FOR CORRECTION OF AMETROPIA

(71) Applicant: The General Hospital Corporation, Boston, MA (US)

(72) Inventors: Richard Rox Anderson, Boston, MA (US); Reginald Birngruber, Luebeck (DE)

(73) Assignee: The General Hospital Corporation, Boston, MA (US)

( * ) Notice: Subject to any disclaimer, the term of this patent is extended or adjusted under 35 U.S.C. 154(b) by 94 days.

(21) Appl. No.: 15/580,976

(22) PCT Filed: Jun. 13, 2016

(86) PCT No.: PCT/US2016/037277
§ 371 (c)(1),
(2) Date: Dec. 8, 2017

(87) PCT Pub. No.: WO2016/201447
PCT Pub. Date: Dec. 15, 2016

(65) Prior Publication Data
US 2018/0177587 A1     Jun. 28, 2018

Related U.S. Application Data

(60) Provisional application No. 62/175,123, filed on Jun. 12, 2015.

(51) Int. Cl.
*A61F 2/14* (2006.01)
*A61F 9/008* (2006.01)
(Continued)

(52) U.S. Cl.
CPC .............. *A61F 2/145* (2013.01); *A61F 2/142* (2013.01); *A61F 2/148* (2013.01); *A61F 9/0017* (2013.01);
(Continued)

(58) Field of Classification Search
CPC .. A61F 9/00812; A61F 9/00834; A61F 2/142; A61F 2/145; A61F 2/1451;
(Continued)

(56) References Cited

U.S. PATENT DOCUMENTS

| 4,298,004 A | 11/1981 | Schachar et al. |
| 5,215,104 A * | 6/1993 | Steinert ................... A61F 9/013 128/898 |

(Continued)

FOREIGN PATENT DOCUMENTS

| DE | 102007023293 | 9/2008 |
| FR | 2819722 | 7/2002 |

(Continued)

OTHER PUBLICATIONS

International Preliminary Report on Patentability in International Application No. PCT/US2016/037277, dated Dec. 12, 2017, 12 pages.

(Continued)

*Primary Examiner* — David H Willse
*Assistant Examiner* — Javier G Blanco
(74) *Attorney, Agent, or Firm* — Fish & Richardson P.C.

(57) ABSTRACT

A method for treating hyperopia or presbyopia in a patient, the method comprising making a cut deep in the patient's cornea to create a two-dimensional slit adjacent to and generally parallel to an anterior surface of the cornea and injecting a liquid or semi-solid transparent filler material into the deep cut in an amount sufficient to flatten the posterior surface of the cornea to increase the refractive power of the cornea by a predetermined correction of up to about 5 diopters due to the physical flattening of the posterior surface of the cornea, wherein the transparent filler
(Continued)

material comprises a refractive index of about 1.3 to about 1.6, and forms a corneal implant with a lenticular shape within the cornea.

17 Claims, 12 Drawing Sheets

(51) Int. Cl.
*A61F 9/00* (2006.01)
*A61F 9/013* (2006.01)
*A61L 27/24* (2006.01)
*A61P 27/10* (2006.01)
*A61L 27/18* (2006.01)
*A61F 9/007* (2006.01)
*A61L 27/20* (2006.01)
*A61L 27/52* (2006.01)

(52) U.S. Cl.
CPC ...... *A61F 9/00736* (2013.01); *A61F 9/00812* (2013.01); *A61F 9/00834* (2013.01); *A61F 9/013* (2013.01); *A61L 27/18* (2013.01); *A61L 27/20* (2013.01); *A61L 27/24* (2013.01); *A61L 27/52* (2013.01); *A61P 27/10* (2018.01); *A61F 2009/00872* (2013.01); *A61F 2210/0085* (2013.01); *A61L 2400/06* (2013.01); *A61L 2430/16* (2013.01)

(58) Field of Classification Search
CPC ............ A61F 2/147; A61F 2009/00872; A61F 9/013; A61F 9/0017; A61L 2430/16; A61L 2400/06
See application file for complete search history.

(56) References Cited

U.S. PATENT DOCUMENTS

| | | | |
|---|---|---|---|
| 5,306,500 A | 4/1994 | Rhee et al. | |
| 5,491,524 A | 2/1996 | Hellmuth et al. | |
| 5,565,519 A | 10/1996 | Rhee et al. | |
| 5,964,748 A | 10/1999 | Peyman | |
| 6,066,170 A | 5/2000 | Lee | |
| 6,814,755 B2* | 11/2004 | LaCombe | A61F 2/142 623/5.14 |
| 8,409,177 B1* | 4/2013 | Lai | A61F 9/008 606/4 |
| 2003/0014042 A1* | 1/2003 | Juhasz | A61F 2/147 606/5 |
| 2004/0015234 A1 | 1/2004 | Peyman | |
| 2006/0216329 A1 | 9/2006 | Peyman | |
| 2008/0039825 A1 | 2/2008 | Lai | |
| 2010/0076417 A1 | 3/2010 | Suckewer et al. | |
| 2011/0098790 A1* | 4/2011 | Daxer | A61F 2/147 607/88 |
| 2011/0319876 A1* | 12/2011 | Feingold | A61F 9/00836 606/4 |
| 2012/0040397 A1 | 2/2012 | Luo et al. | |
| 2012/0238904 A1 | 9/2012 | Manns et al. | |
| 2012/0267510 A1 | 10/2012 | Gross et al. | |
| 2013/0053952 A1* | 2/2013 | Jun | A61F 2/142 623/5.11 |
| 2014/0012240 A1 | 1/2014 | Ho et al. | |
| 2015/0290030 A1 | 10/2015 | Suckewer et al. | |

FOREIGN PATENT DOCUMENTS

| | | |
|---|---|---|
| WO | 2008/055118 | 5/2008 |
| WO | WO 2011/029095 | 3/2011 |
| WO | WO 2014/198406 | 12/2014 |
| WO | WO 2017/210374 | 12/2017 |

OTHER PUBLICATIONS

Extended European Search Report in Application No. 16808532.2, dated Jun. 15, 2018, 11 pages.
International Search Report and Written Opinion dated Oct. 4, 2016 in international application No. PCT/US2016/037277, 14 pgs.
Binder "Intracorneal inlays for the correction of presbyopia and low hyperopia," Ophthalmology Times Europe, Dec. 1, 2015.
International Preliminary Report on Patentability in International Application No. PCT/US2017/035333, dated Dec. 13, 2018.
International Search Report and Written Opinion in International Application No. PCT/US2017/035333, dated Aug. 3, 2017.
Olsen, "On the calculation of power from curvature of the cornea," British Journal of Ophthalmology, 70, 152-154 (1986).
Winkler "Nonlinear optical macroscopic assessment of 3-D corneal collagen organization and axial biomechanics," I OVS, vol. 52, 8818-8827, 2011.

* cited by examiner

CORNEAL FILLERS FOR CORRECTION OF AMETROPIA

CROSS-REFERENCE TO RELATED APPLICATION

This application is a U.S. National Phase Application under 35 U.S.C. § 371 of International Patent Application No. PCT/US2016/037277, filed on Jun. 13, 2016, which claims priority from U.S. Provisional Application No. 62/175,123, filed on Jun. 12, 2015, the contents of both of which are incorporated herein by reference in their entireties.

FIELD OF THE INVENTION

The invention relates to corneal fillers for correction of ametropia.

BACKGROUND OF THE INVENTION

Ametropia refers to significant refractive errors of the eye. Light is focused onto the retina mainly through a combination of refraction by the cornea-air interface, and through the ocular lens. Accommodation (adjusting the eye's focus) occurs through changes in the lens, which fine-tune the refractive power of the eye. Approximately 42 diopters (dpt) of the total refractive power of about 60 dpt of the eye is due to the curvature of the cornea, which does not change during accommodation. Ametropia includes myopia (near-sightedness), hyperopia (farsightedness), and astigmatism (cylindrical and other aberrations). All forms of ametropia can be corrected at least partially, by glasses or contact lenses.

Surgical corrections vary with the kind of ametropia. Most people with ametropia have myopia, which is surgically corrected by reducing the curvature of the cornea. Laser-Assisted in situ Keratomileusis (LASIK), photorefractive keratotomy (PRK), and similar techniques remove a thin lenticular layer of tissue from within the stroma of the central cornea, reducing its outer curvature. LASIK is by far the most frequently used technique. A laminar cut is made in the stroma using a microtome or a short pulsed laser, which creates a thin flap that remains attached at one edge. When a laser is used to create the flap, cutting is carried out by a scanning laser focused within the corneal stroma, followed by a ring-shaped cut through the outer surface of the cornea. The opened flap exposes the cornea stroma. An excimer laser is then used to remove a precise, lenticular-shaped, thin layer of cornea tissue, followed by closing the flap, which re-attaches by adhesion. The pattern and amount of tissue removed is precisely determined to produce the desired reduction in cornea curvature. Astigmatism can also be corrected by LASIK.

Novel, but not yet approved refractive procedures like ReLEx® (Refractive LEnticule Extraction), e.g., femtosecond lamellar extraction (FLEx), and SMILE (SMall Incision Lenticule Extraction) remove stromal lenticule by using femtosecond laser surgery, which is able to make precise cuts within the cornea without damage to the surface of the cornea. Radial keratotomy and similar techniques that injure the cornea in a peripheral pattern, reducing the central cornea curvature after healing, are highly invasive and not predictable enough and therefore not currently employed. For hyperopia correction, LASIK, radial keratotomy and similar techniques either do not work well, or at all.

To correct hyperopia, it is known that the curvature of the surface of the cornea must be increased. A variety of corneal rings have been devised to treat hyperopia. The early corneal rings were made from sutures, which acted like a purse string around the central cornea. An annular cut is made into the cornea around its central axis, and the ring is embedded into the stroma. By tightening or otherwise adjusting the ring, tension is partially relieved on the central cornea, causing its curvature to increase. Unfortunately, corneal rings are problematic compared with LASIK. A substantial injury is produced, the ring typically requires multiple adjustments, tension is concentrated at the ring itself, the degree of correction is difficult to predict, and it is difficult to correct astigmatism. Corneal rings pose so many problems that most patients with hyperopia elect not to use them.

SUMMARY OF THE INVENTION

This disclosure provides transparent corneal fillers and methods to use these fillers to correct vision distorted by ametropia, in particular hyperopia and presbyopia. In the new methods, a two-dimensional small incision is created deep below the corneal surface, within the stroma of the cornea, e.g., with a pulsed laser. The cornea remains largely intact when the laser cutting is performed, but for a two-dimensional slit that extends over a circular or oval-shaped region over the central cornea responsible for refraction of light within the pupillary area of the eye. The cutting includes a cut within the bottom 50% or so of the thickness of the cornea, e.g., ranging from about the bottom 10, 15, 20, 25, 30, 35, 40, 45, or 50% of the thickness of the cornea, e.g., in a region about 50-250 µm from the bottom, or posterior, surface of the cornea.

A transparent filler material is then injected into the space created by the cut. The present disclosure is based on the discovery, inter alia, that when a filler material is injected deep within the cornea, the injected material forms the shape of a lenticule, i.e., a lens having a convex surface facing the outer surface of the cornea and a concave surface facing the inner surface of the cornea. The amount of the filler material injected is sufficient to cause the interior surface of the cornea to be flattened. This physical flattening of the inner (or posterior) surface of the cornea when the filler material has a refractive index that is about the same as the refractive index of the cornea, which is about 1.376, e.g., when the filler material has a refractive index of about 1.35 to about 1.39 or about 1.36 to about 1.38, then the physical flattening of the inner surface of the cornea itself causes an overall refractive correction of about 4.0 to 5.0 diopters, e.g., 4.1, 4.3, 4.5, 4.7, or 4.9 diopters.

On the other hand, if the injection is made into a slit created near the anterior or outer surface of the cornea, e.g., a superficial 2D cut or slit, the filler material raises the corneal surface overlying the filler, thus increasing the curvature of the outer surface of the cornea. In addition to the described geometrical changes of the corneal surfaces the formed lenticular filler participates in the refractive change if the filler material has a refractive index different from that of the cornea. For example, for the deep cut, if the refractive index of the filler material is higher than that of the cornea, e.g., about 1.4 to 1.6, e.g., about 1.5, e.g., 1.45 to 1.55, or 1.53 to 1.58, and the amount of filler material is sufficient to flatten the interior surface of the cornea, then the lenticular-shaped filler material itself can add an additional refractive change of about 10 to 25 diopters, e.g., about 12 to 23 diopters, 14 to 21 diopters, 15 to 20 diopters, or 16 to 18 diopters.

In both injection locations, or with a combination of both injection locations, the result is correction of the diagnosed ametropia, e.g., hyperopia and/or astigmatism.

A deep corneal cut results in a fine-tunable, precise increase in refractive power of the cornea. Because of the "quietness" of the inner corneal surface a sophisticated re-shaping of that surface can be achieved that is stable in the long term. For instance, a bifocal shape can be created to correct presbyopia. An intentional modification of the inner surface of the cornea for hyperopia treatment provides a correction of up to about 5 diopters or a combination of anterior and posterior surface modification is feasible and particularly advantageous.

In one aspect, the disclosure features a method for treating hyperopia or presbyopia in a patient, the method comprising making a cut deep in the patient's cornea to create a two-dimensional slit adjacent to and generally parallel to an anterior surface of the cornea. and injecting a liquid or semi-solid transparent filler material into the deep cut in an amount sufficient to flatten the posterior surface of the cornea to increase the refractive power of the cornea by a predetermined correction of up to about 5 diopters due to the physical flattening of the posterior surface of the cornea, wherein the transparent filler material comprises a refractive index of about 1.3 to about 1.6, and forms a corneal implant with a lenticular shape within the cornea.

Some aspects of the disclosure include that the deep cut is made at a depth of greater than 300 microns from the anterior surface of the cornea. The deep cut is made at a depth of greater than 400 microns from the anterior surface of the cornea. The transparent filler material comprises a liquid filler material. The transparent filler material is not cured or crosslinked so that it maintains a liquid consistency. The transparent filler material comprises a hydrogel filler material. The filler material comprises a refractive index greater than about 1.4 and causes an additional increase in the refractive power of the cornea due to the lenticular-shaped filler material itself of about 10 to 25 diopters.

In further aspects of the disclosure the method includes making a second, superficial cut in the patient's cornea to create a two-dimensional slit adjacent to and generally parallel to an anterior surface of the cornea, and injecting a liquid or semi-solid transparent filler material into the superficial cut in an amount sufficient to increase the curvature of the anterior surface of the cornea to increase the refractive power of the cornea by a predetermined correction of up to about 12.0 diopters due to the physical increased curvature of the anterior surface of the cornea, wherein the transparent filler material forms a corneal implant with a lenticular shape.

The method can also include that the filler material comprises a refractive index greater than about 1.4 and causes an additional increase in the refractive power of the cornea due to the lenticular-shaped filler material itself of about 10 to 25 diopters. The combined refractive power of the change in curvature of the posterior and/or anterior surface of the cornea and the refractive power of the lenticular-shaped filler material itself is sufficient to avoid the need for an intraocular lens (IOL) after cataract extraction. Cutting the cornea comprises cutting a two-dimensional (2D) slit centered on an optical axis of the cornea. The slit is a circularly shaped 2D slit to correct spherical hyperopia. The slit is a non-circularly oval shaped 2D slit to correct hyperopic astigmatism. The cutting is performed by a laser.

In some aspects of the disclosure the method includes solidifying the filler material after injecting the filler material to form a solid or semi-solid corneal implant. Solidifying the filler comprises crosslinking the filler. The filler material is crosslinked by light exposure. The filler material is crosslinked by the addition of a photo-crosslinking agent and light exposure. The solidified filler material forms a corneal implant that is highly viscous. The filler material comprises a non-immunostimulatory filler material. The corneal implant has a uniform refractive index. The corneal implant has a refractive index of about 1.3 to 1.5, 1.33 to 1.4, or 1.36 to 1.39. The filler material comprises one or more of crosslinked hyaluronic acid (HA), dilute collagen fibrils, collagen gel, and silicone. The filler material comprises ribose-crosslinked HA. The filler material is injected to create a bifocal shape.

In further aspects of the disclosure, the method comprises fixing the corneal implant in place within the corneal cut. The corneal implant is fixed in place by crosslinking components of the filler material to corneal tissue. The corneal implant is fixed in place by applying a crosslinking agent to an internal surface of the corneal cut. The crosslinking agent is injected into the corneal cut before the filler material is injected into the corneal cut. After the filler material is injected into the corneal cut, the crosslinking agent is activated to cause the filler material to crosslink to corneal tissue at an interface between the filler material and the corneal cut. The method includes solidifying the filler material. The crosslinking agent is injected into the corneal cut after the filler material is injected and crosslinked to form the corneal implant. Activating the crosslinking agent to crosslink the filler material to corneal tissue at an interface between the filler material and the corneal cut. The crosslinking agent is mixed into the filler material and further comprising crosslinking the filler material and simultaneously crosslinking a component of the filler material to corneal tissue at an interface between the filler material and the corneal cut.

In further aspects described is use of a liquid or semi-solid transparent filler material for treating hyperopia or presbyopia by making a cut deep in the patient's cornea to create a two-dimensional slit adjacent to and generally parallel to an anterior surface of the cornea, and injecting the filler material into the deep cut in an amount sufficient to flatten the posterior surface of the cornea to increase the refractive power of the cornea by a predetermined correction of up to about 5 diopters due to the physical flattening of the posterior surface of the cornea, wherein the transparent filler material comprises a refractive index of about 1.3 to about 1.6, and forms a corneal implant with a lenticular shape within the cornea.

Also described is a liquid or semi-solid transparent filler material for treating hyperopia or presbyopia by making a cut deep in the patient's cornea to create a two-dimensional slit adjacent to and generally parallel to an anterior surface of the cornea, wherein the transparent filler material is injectable into the deep cut in an amount sufficient to flatten the posterior surface of the cornea to increase the refractive power of the cornea by a predetermined correction of up to about 5 diopters due to the physical flattening of the posterior surface of the cornea, wherein the transparent filler material comprises a refractive index of about 1.3 to about 1.6, and forms a corneal implant with a lenticular shape within the cornea.

As used herein, the term "ametropia" means a condition of the eye in which images fail to come to a proper focus on the retina, due to a discrepancy between the size and refractive powers of the eye or the astigmatic shape of the refractive power of the eye.

As used herein, the terms "refractive index" or "index of refraction" refer to the dimensionless number that describes how much light is bent or refracted when crossing the interface between two materials, such as at the interface between air and the cornea or between the cornea and an injected filler material in the shape of a lenticule.

As used herein, the phrase "in the shape of a lenticule" or "lenticular-shaped" when referring to the shape of a filler material injected into a planar, 2D slit within the cornea, means that the amount of the filler material injected into the slit is sufficient to expand the slit into the form of a lens that has a convex surface facing the outer surface of the cornea and a concave surface facing the inner surface of the cornea. For a deep cut or slit in the cornea, this sufficient amount of filler material is achieved when the injected filler material flattens the inner surface of the cornea.

As used herein, the terms "superficial" and "deep" when referring to a cut or slit in the cornea refer to cuts or slits made at depths that we within the top 50% or bottom 50% of a cornea, respectively, which in humans is typically about 0.5 mm thick.

The methods described herein provide several advantages including providing a minimally-invasive, long-lasting, well-tolerated method for correcting hyperopia. Unlike LASIK, the corneal filler and methods of use described herein do not create a free flap. Its use therefore reduces the likelihood that the treated eye will be more sensitive to subsequent injury, compared with LASIK-treated eyes. The flap created during LASIK surgery remains poorly attached for tens of years, and can be sheared away if something strikes the cornea such as water during a high dive. With the corneal implant the outer cornea-air interface is not changed by the deep cut and injected filler material, or if a superficial cut is also made, then the outer surface of the cornea is uniformly raised, and the curvature increases, but without any point of high stress, unlike the high stress that occurs at the site of corneal ring placement. Unlike LASIK, or corneal rings, or radial keratotomy, the correction made is reversible and easily adjustable.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

General Methods of Using Corneal Fillers

Figure 1A:
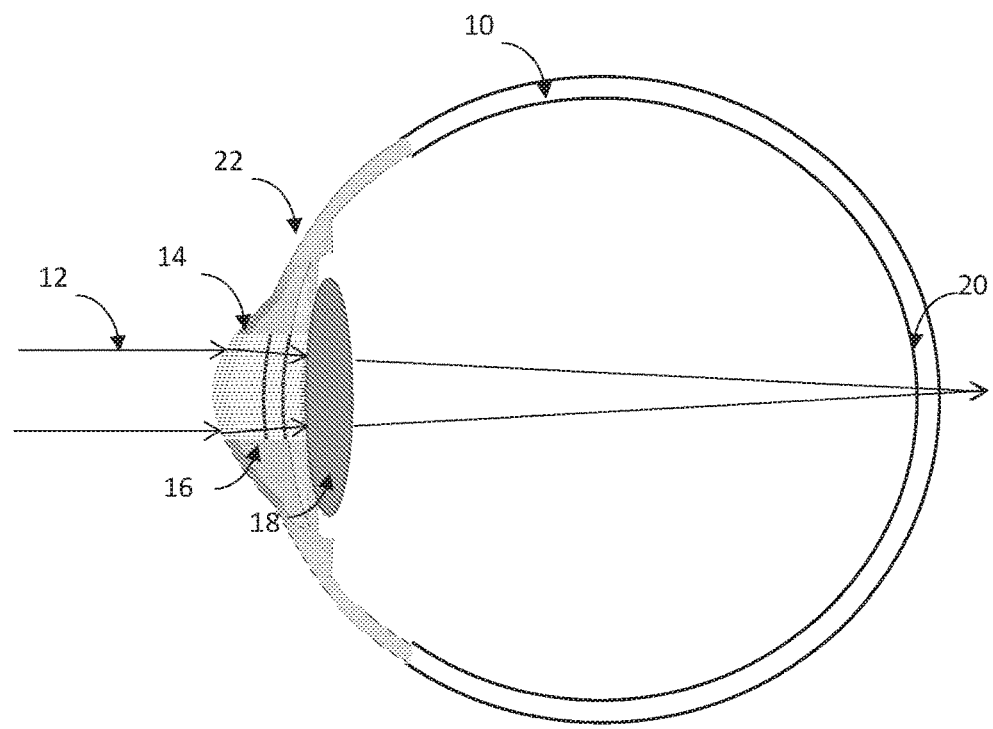
FIGS. 1A and 1B are schematic drawings showing light travelling through a hyperopic eye and light travelling through a hyperopic and corrected eye.

In the new methods, a transparent corneal filler is used to correct vision distorted by ametropia. In general, to perform this correction, a two-dimensional ("2D") cut or slit is created deep inside the cornea, within the stroma of the cornea, e.g., with a pulsed laser. Such lasers have been used in eye surgery before and are well described (e.g., LASIK); the laser is typically a femtosecond, picosecond or nanosecond pulsed near-infrared or ultraviolet laser. In the methods described herein a small, or no, incision through the cornea surface is needed, and no corneal flap is ever created. In this regard, the cornea remains more intact than after LASIK, and much more intact than after corneal ring placement. The laser cutting is performed at a depth within the bottom 50% of the cornea thickness, ranging from about 250 to 450 µm deep, e.g., 300 to 450 µm deep or 350-400 µm deep (measured from the anterior or outer surface of the cornea), and extending over a circular or oval-shaped region that extends over much, if not all, of the central cornea responsible for refraction of light along the visual axis of the eye. The diameter of this intra-cornea cutting is approximately 3 to 9 mm, e.g., 4 to 8 mm, or 5 to 6 or 7 mm.

A transparent cornea filler material is injected into the virtual space (two-dimensional cut) created by the laser cutting. A fine needle is used, typically inserted into the edge of the cutting space, with very minimal trauma to the cornea. A volume of filler is added that is sufficient to flatten the inner (posterior) corneal surface. The filler decreases the cornea's curvature on the posterior surface at the central axis in a controlled manner, resulting in appropriate correction of hyperopia. In addition, a second, more superficial cut can be made that when injected with a filler material (either the same or different from the filler material injected into the deep slit) increases the curvature of the anterior (outer) surface of the cornea to produce a greater overall vision correction.

When the filler material is injected into the deep cut, the posterior surface flattens, which leads to an increased refractive power of the cornea. The flattened and therefore decreased negative optical power of the inner cornea surface can contribute to the total power of the cornea up to about 4 to 5 diopters, e.g., 4.1, 4.2, 4.3, 4.4, 4.5, 4.6, 4.7, 4.8, or 4.9 diopters.

By utilizing a deep corneal cut it is possible to fine-tune, and precisely increase the refractive power of the cornea. Because of the "quietness" of the inner corneal surface a more sophisticated reshaping of that surface is possible and is quite stable in the long term. A typical example of such a sophisticated re-shaping is the correction of presbyopia, where a bi-focal shape of the inner corneal surface is required. This bi-focal shaping can be achieved either by injecting a sufficient amount of filler material into a small corneal cut or by injecting a filler material into a deep annular or ring-shaped corneal cut. An intentional modification of the inner surface of the cornea for hyperopia treatment up to 4.5 or 5 diopters or a combination of anterior and posterior surface modification is particularly advantageous. In addition, by using a filler material with a refractive index higher than that of the cornea, an even greater refractive correction can be achieved, e.g., up to about a total of about 30 diopters. For example, for the deep cut, if the refractive index of the filler material is higher than that of the cornea, e.g., about 1.4 to 1.6, e.g., about 1.5, e.g., 1.45 to 1.55, or 1.53 to 1.58 (e.g., if the filler material is a silicone oil or silicone oil gel), and the amount of filler material is sufficient to flatten the interior surface of the cornea, then the lenticular-shaped filler material itself can add an additional refractive change of about 10 to 25 diopters, e.g., about 12 to 23 diopters, 14 to 21 diopters, 15 to 20 diopters, or 16 to 18 diopters, which when added to the change caused by the flattening, provides an overall refractive correction of about 14 to 30 diopters, e.g., 16 to 28 diopters, 18 to 26 diopters, 20 to 24 diopters. In some circumstances, such a correction can avoid the need to implant in inter-ocular lens ("IOL") after surgery to remove a cataract (a cloudy lens).

If astigmatism is also to be corrected, the shape of the laser cutting can be made ovoid rather than circular, with the long axis of the oval oriented across the axis of astigmatism. A bifocal shape can be created to correct presbyopia. Thus, both astigmatism and hyperopia can be simultaneously corrected.

Detailed optical analysis shows that the total corneal refraction consists of two refractive parts, the anterior refraction (between the air and superior or anterior corneal surface) which is about 48 diopters (dpt) and the posterior part (between the posterior or inner corneal surface and the anterior chamber fluid surface) that is about −5 dpt, resulting in the total corneal refraction of about 43 dpt. If the filler material is injected into a deep cut, the posterior or inner surface of the cornea flattens, which leads to an increased refractive power of the cornea. In addition, if one adds a superficial cut and injects a filler material, then the anterior or outer surface of the cornea bulks out and causes an increase in the refractive power of the cornea. Therefore, according to the present disclosure, both refractive changes need to be taken into account.

The flattened and therefore decreased negative optical power of the inner cornea surface can contribute to the total optical power of the cornea up to about 4.5 or 5 diopters. The advantage of manipulating this posterior or inner surface of the cornea to provide a refractive power correction is threefold: first, it can be easily fine-tuned, because the relation between the refractive power change and the curvature change is weaker than that of the anterior surface. Second, the inner surface of the cornea is a much "quieter" region than the outer region and is not distorted by uncontrolled epithelial growth, tear film inhomogeneities, blinking forces, etc. Third, a deeply positioned corneal filler should not weaken the corneal stability against stromal degradation (corneal melting).

FIGS. 1A and 2B illustrate the path of light through the eye 10. Incoming light 12 that is incident on the eye 10 is refracted (its direction changed) as it passes through the cornea 14, aqueous chamber 16, and lens 18 such that the refracted light rays converge on a focal point F. In the hyperopic or farsighted eye shown in FIG. 1A, the focal point F is behind the retia 20, leading to blurry vision and the need for correction. In the eye corrected by a corneal implant 100, shown in FIG. 1B, the amount of refraction of the incoming light 12 has been reshaped so that the focal point $F_1$ has been corrected to be on the retina 20.

Figure 2:
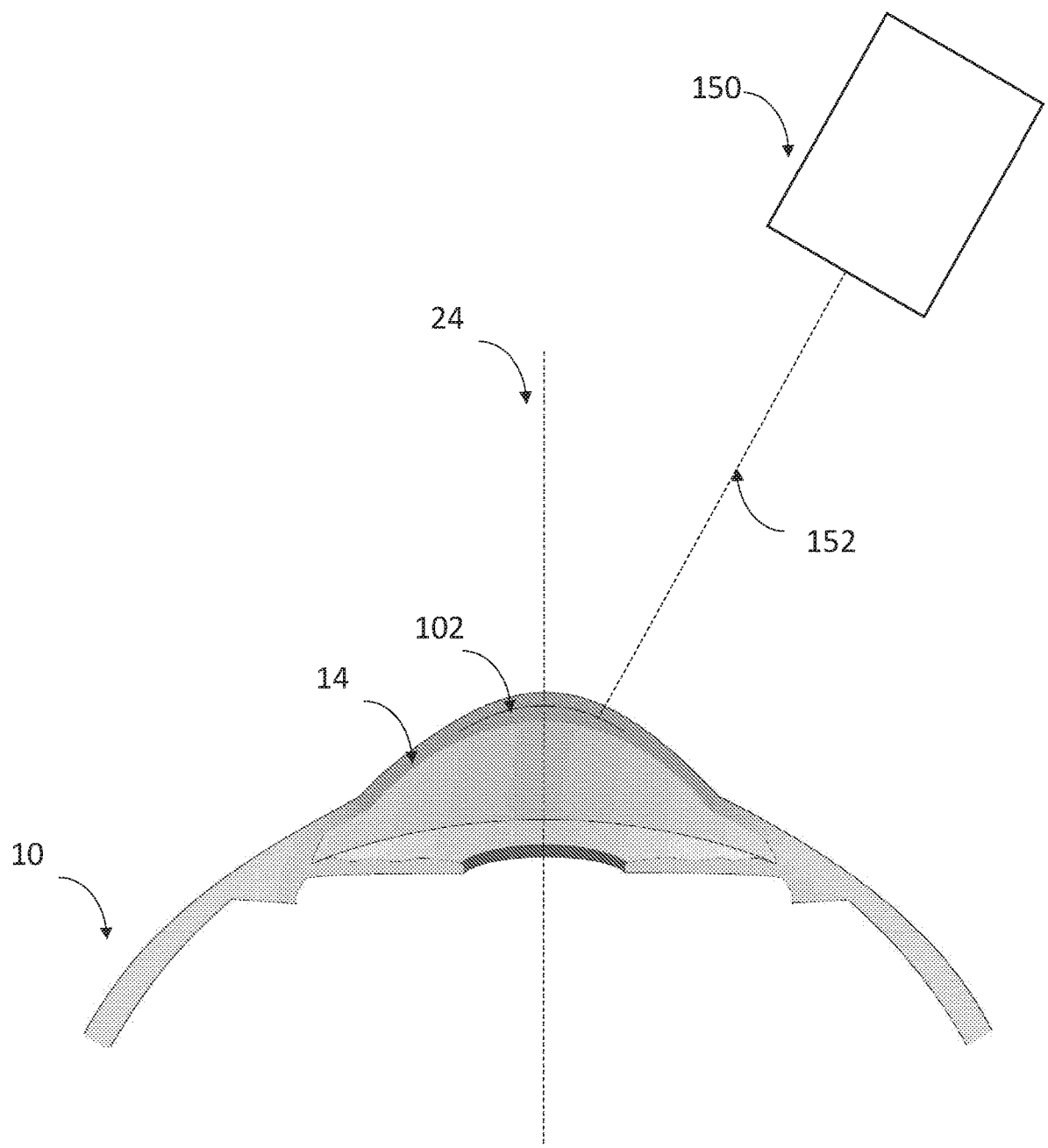
FIG. 2 is a schematic drawing showing a controlled slit being created within a cornea.

A first step in implanting a corneal implant 100 involves laser cutting of the interior of the cornea 14. This laser cutting is of the type currently used in refractive surgery flap preparation which cuts the cornea 14. As illustrated in FIG. 2, a surgeon makes a highly precise two-dimensional (2D) cut 102 deep within the cornea 14 using a laser 150. The laser 150 can be a femtosecond laser. This laser-cutting technique allows the laser 150 to make a cut internally within the cornea 14 with laser beam 152 without cutting the outer surface or sides of the cornea. No flap is created, the inner part of the cornea is not exposed to ambient air, and the corneal surface remains intact. In other embodiments, a small incision can be made through the cornea to inject the corneal filler.

For example, a 5-9 or 6-8 mm diameter 2D slit or cut 102 can be made within the central part of the cornea 14, intersecting its central axis. The cut 102 is made at a certain depth into the bottom half of the cornea. For example, the cut 102 can be made in the bottom 250 μm of the approximately 500 μm-thick cornea 14. The cut 102 separates the cornea into a top part 14a of the cornea 14 and a bottom part 14b of the cornea 14 (shown more clearly in FIG. 4). The top part 14a of the cornea can be more than half of the corneal thickness. The cornea remains largely intact, because there is no open flap created.

In other embodiments a deep ring-shaped corneal cut, centered at the optical axis 24 of the eye is made with the laser 150 in order to allow the injection of an annularly shaped implant 100 to create a bi-focal inner surface of the cornea for correction of presbyopia.

Figure 3:
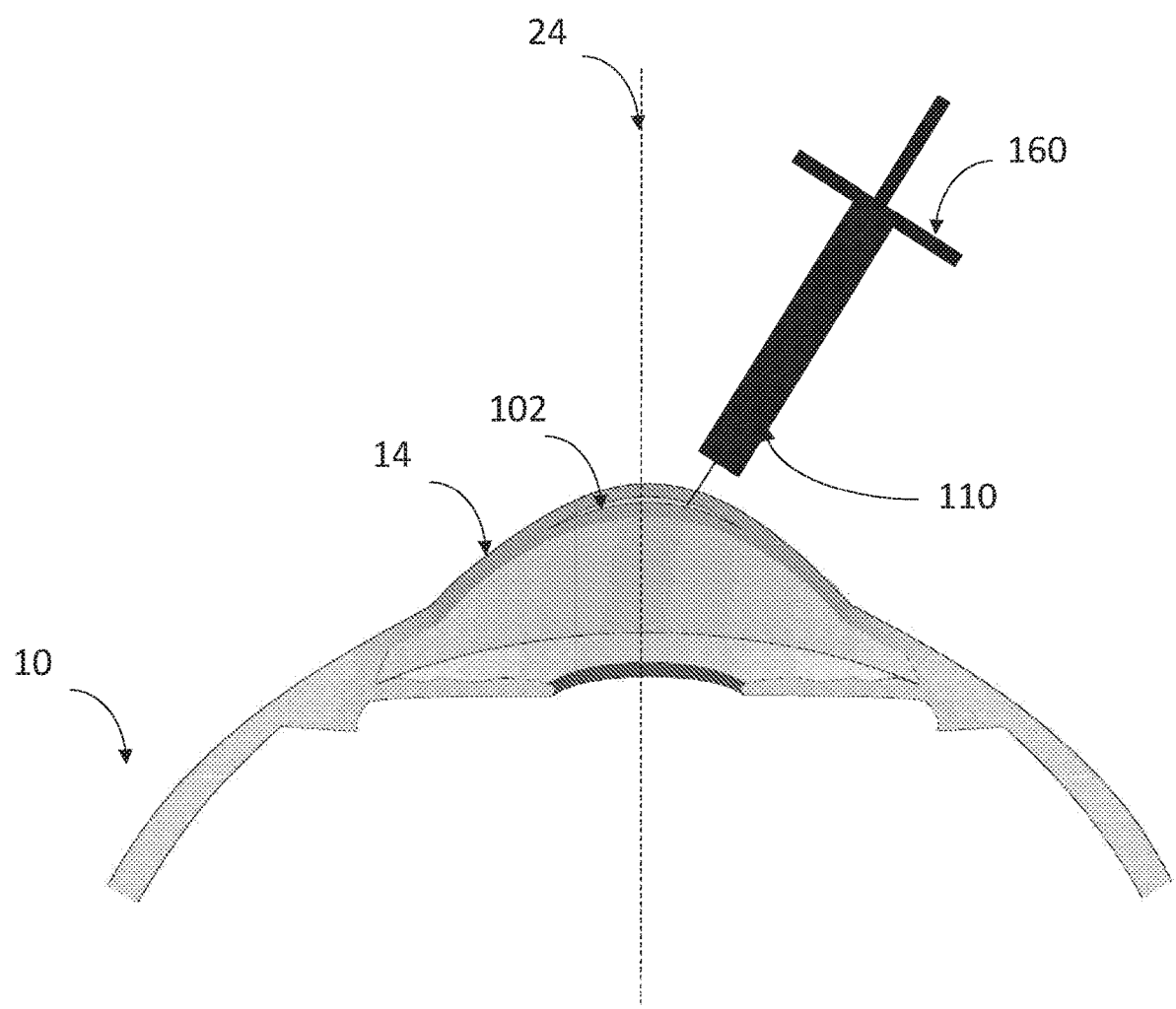
FIG. 3 is a schematic drawing showing a filler material being injected into the slit in the cornea shown in FIG. 2.

As shown in FIG. 3, the surgeon then injects the filler material 110, in liquid form or semi-liquid form, through a syringe 160 with a fine needle. The filler material 110 can be injected by piercing the outer layers of the cornea 14 with the needle 160, or via a tiny intra-stromal channel made through the cornea 14. In some embodiments that channel can be created with a step (e.g., a zig-zag, or a valve configuration), so that when the filler material is injected, the internal pressure it creates tends to seal the channel. Alternatively, the channel can be sealed with a tissue adhesive or glue, or a stitch made in the corneal surface to prevent the filler material from leaking out of the slit through the channel.

Figure 4:
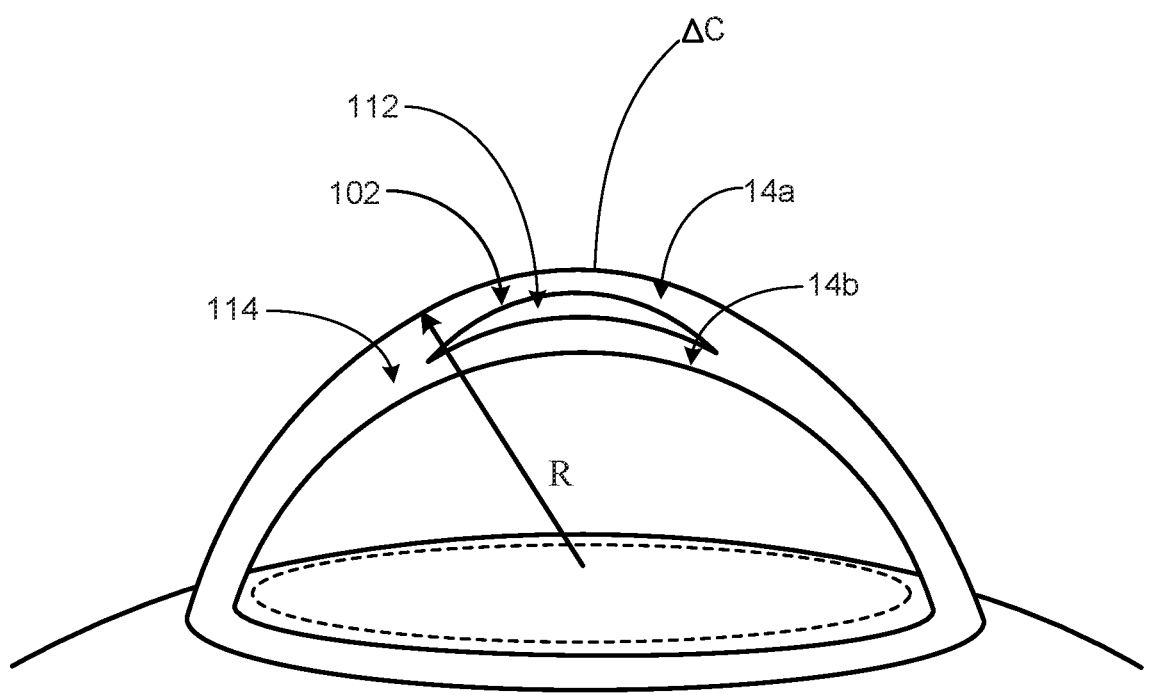
FIG. 4 is a perspective schematic illustrating the new corneal shape due to the injection of the filler of FIG. 3.
Figure 5A:
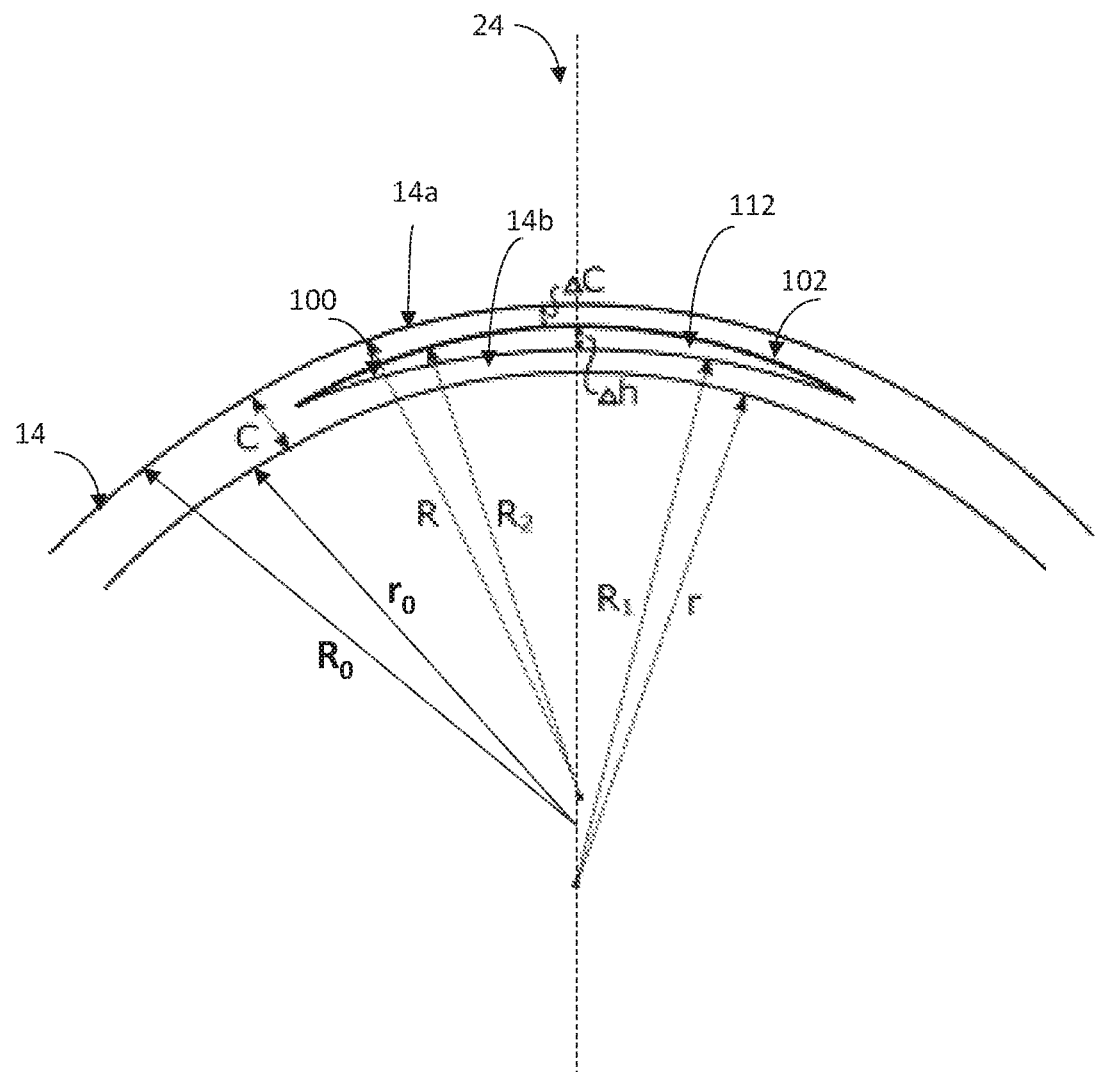
FIGS. 5A-5B are close ups on the implanted cornea of FIG. 4 illustrating the spatial relationships due to the corneal implant implanted deeply, and to corneal implants implanted deeply and superficially within the cornea, respectively.
Figure 5B:
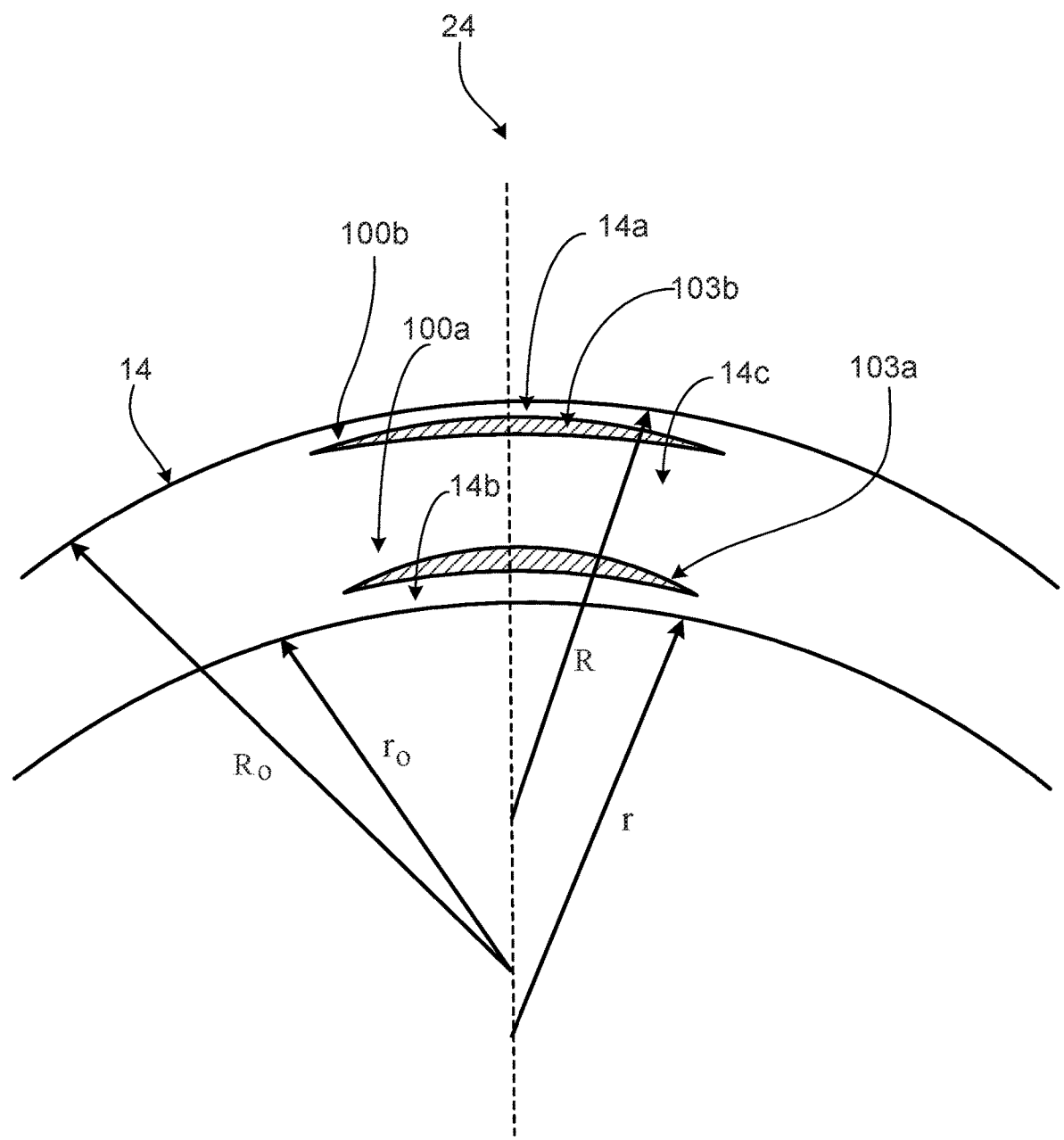

As shown in FIG. 4 and FIGS. 5A and 5B, the filler material 110 is added with a specified quantity of added filler 112 injected into the cut 102. As discussed below, the volume is finely controlled to result in a specific change of refraction $\Delta F$. This filler addition causes the bottom part 14b of the cornea 14 to flatten inwardly to accommodate the increased volume. Once adapted and fixed in place, the added filler 112 becomes a semi-permanent corneal implant 100 that adds a lenticular-shaped, transparent volume above the posterior surface of the cornea. Adaptation of the filler material may be necessary to, depending on the filler material, exchange water and other molecules between filler and corneal stroma.

The corneal implant 100 increases the overall thickness of the cornea 14 at the optical axis 24 of the eye 10 more than at the edges of the cut region, in a lenticular shape. Along the central optical axis 24 the corneal implant 100 has a maximum height Δh, and the height decreases down to zero as you travel outwards from the optical axis 24. As shown specifically in FIG. 5A, implantation of the corneal implant 100 deep within the cornea causes the bottom surface of the cornea to flatten. The top part 14a of the cornea 14 has a thickness ΔC that is approximately uniform across the area of the corneal implant 100. The original thickness C of the cornea 14 is unchanged at the edges of the cornea, radially distant from the corneal implant and the central optical axis 24. However the thickness of the cornea within the implant area is increased, being a total of the thickness of the bottom part 14b of the cornea, the height of the corneal implant (which changes due its lenticular shape and is its max Δh at the central optical axis 24 of the implant) and height ΔC of the top part 14a of the cornea (which is uniform over the corneal implant 100).

Consequently, the radii of curvature of the cornea also change due to the corneal implant 100. Prior to implantation, the cornea 14 had an overall original anterior radius of curvature $R_0$ (with respect to the cornea-air interface), and posterior radius of curvature $r_0$ (with respect to the cornea-anterior chamber interface). This original anterior radius of curvature $R_0$ remains the same in the corrected eye at positions distant from the corneal implant 100 (e.g., at the location shown in FIG. 5A). For relatively deep cuts (e.g., cuts made near the posterior surface of the cornea), the posterior radius of curvature $r_0$ changes to a second radius of curvature $r_1$ as well as the radius of curvature $R_1$ to the location of the bottom of the cut 102 and bottom of the implant 100.

Figure 1B:
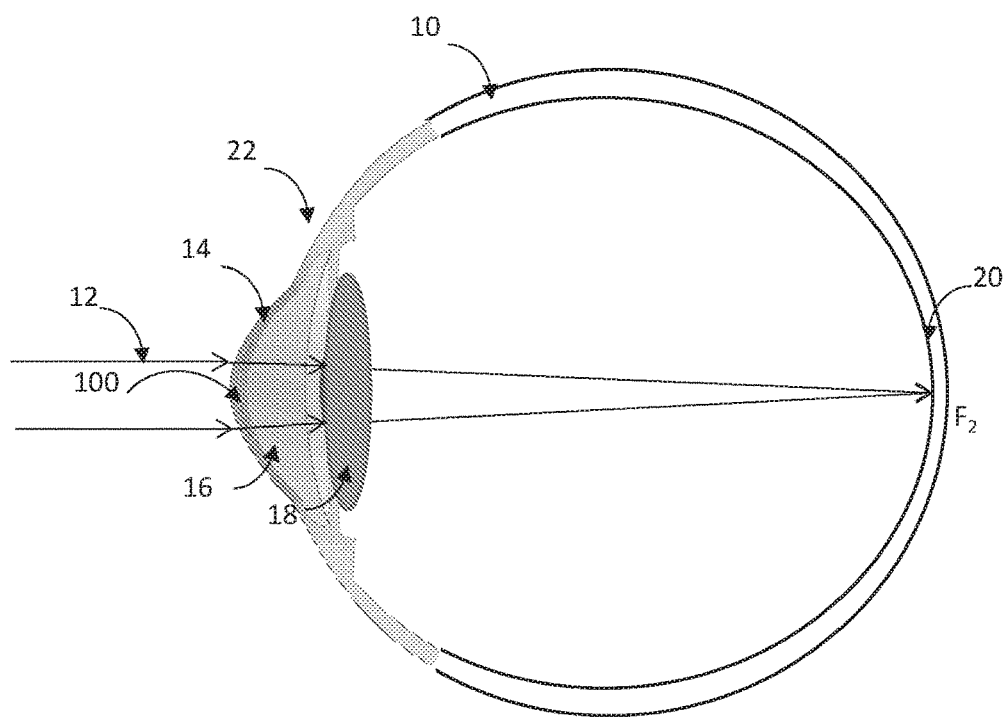

Due to the implant 100, the original radius of curvature $R_0$ of the cornea is changed in the central area of the cornea, becoming adjusted overall radius of curvature R. The radius of curvature $R_2$ to the top of the corneal implant, as well as of the overall anterior radius of curvature cornea, are unchanged as only the inside surface is changed. The decrease in radius of curvature correlates with an increase in curvature, yielding the eye correction due to movement of the focal point from $F_1$ to on the retina 20 at $F_2$ (as shown in FIGS. 1A and 1B).

As shown in FIG. 5A, the radii of curvature of the cornea also change due to the corneal implant 100 being inserted into a superficial portion of the cornea. Prior to implantation, the cornea 14 had an overall original anterior radius of curvature $R_0$ (with respect to the cornea-air interface), and posterior radius of curvature $r_0$ (with respect to the cornea-anterior chamber interface). This original anterior radius of curvature $R_0$ remains the same in the corrected eye at positions distant from the corneal implant 100 (e.g., at the location shown in FIG. 5A). The anterior radius of curvature at positions within the corneal implant 100 however decreases to R. For relatively superficial cuts (e.g., cuts made near the anterior surface of the cornea), the posterior radius of curvature r remains unchanged as does the radius of curvature $R_1$ to the location of the bottom of the cut 102 and bottom of the implant 100. Such implants can change the total optical power of the cornea up to about 12 dpt when using a filler material that has a refractive index that is about the same as that of the cornea. Of course, if a filler material is used that has a refractive index higher than that of the cornea, e.g., about 1.4 to 1.6, e.g., a silicone oil, then the total refractive change can be even greater, e.g., up to about 22 to 37 diopters.

Figure 6:
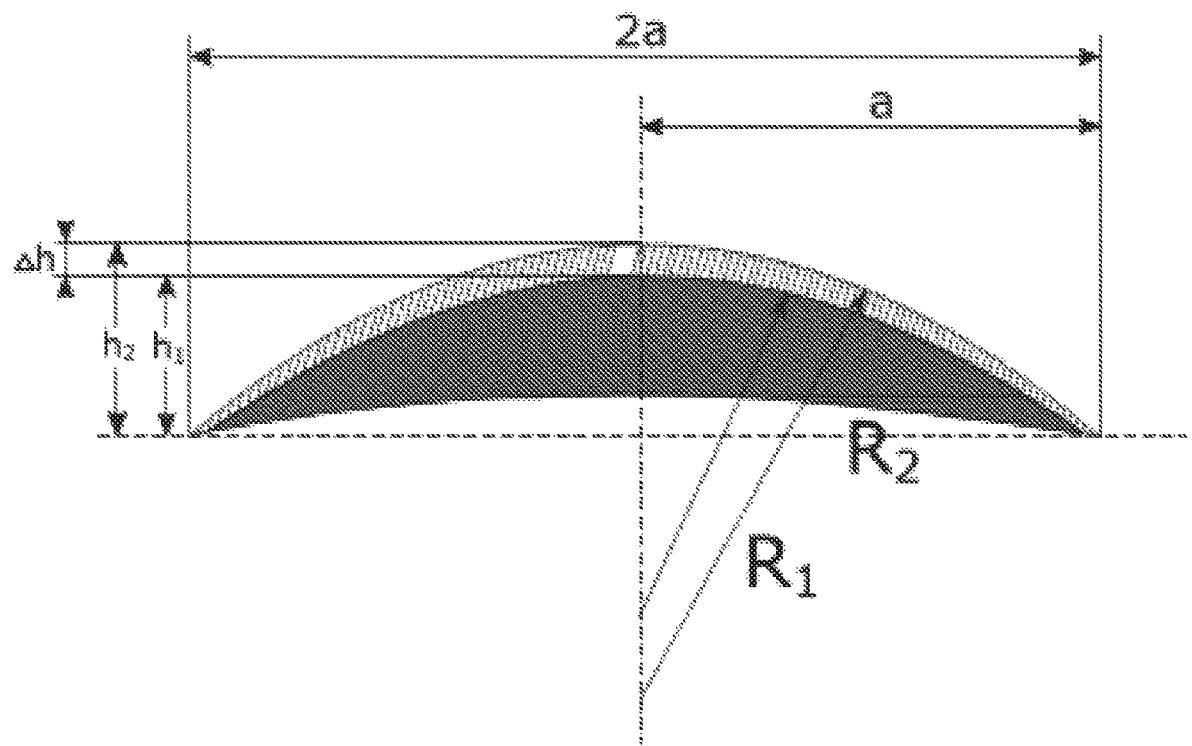
FIG. 6 is a perspective side view of a corneal implant.

FIG. 6 illustrates the lenticular shape of the corneal implant 100. The corneal implant 100 has a diameter 2a, and half diameter a. The maximum height Δh is the difference from the distance to the bottom of the implant $h_1$ (equal to the implant-top of the cornea 14b interface) and the top of the implant $h_2$ (equal to the implant-bottom of the cornea 14a interface) along the optical axis 24, and is correlated with the radii of curvature $R_1$, $R_2$. The maximum height Δh is typically in the range of 10-400 μm and the diameter 2a of the corneal implant 100 is typically in the range of 5-8 mm (e.g., approximately 6 mm). Adjustment of diameter 2a, maximum height Δh, and volume ΔV of added filler 112 can be selected to refract the light differently and yield different changes in the focal length ΔF.

In general, adding a greater volume of filler matter 110 yields a greater amount of refractive correction. An accurate, predicable correction can be achieved for deep corneal cuts (without changing the anterior surface of the cornea) in the range from about 0-5 dpt, which can be used to correct the vision of the vast majority of people with hyperopia. To determine the precise size and shape of the cut 102 and the volume ΔV of the added filler 112 injected to correct a particular hyperopia, the surgeon can rely on models that correlate the amount of refractive error correction with the volume ΔV of added filler 112, the diameter 2a of the intra-cornea cut 102, the final refractive index and the final central thickness Δh of the corneal implant 100.

It is particularly beneficial to obtain desired corrections with a central thickness Δh of the corneal implant 100 in the range of about 0-400 μm implanted deep within the cornea near to the posterior surface. For example, as shown in Table 1 for a corneal implant with diameters ranging between 2a=5 mm and 2a=8 mm and an anterior corneal thickness ΔC of 300 μm, the refractive change of the cornea desired can be obtained by a corresponding flattened radius $R_1$=7.53 mm to $R_1$ of the bottom of the implant by changing the volume of the cornea ΔV due to the added filler 112. An uncorrected eye with no corneal implant 100 that has no change in focal power ΔF and no added corneal volume ΔV due to the added filler 112 has a radius of curvature $R_1$ of approximately 7.53 mm. A change of 1 dpt in focal power can be obtained with an adjusted radius of curvature $R_1$ of 9.09 mm that corresponds to an added corneal volume ΔV of approximately 1.7 μl for an diameter of 2a=6 mm, for example. A correction of 5 dpts (the range required for the majority of hyperopic patients) correlates to a new $R_1$ of 80.20 mm and ΔV of 8.1 μl for a corneal diameter of 2a=6 mm.

TABLE 1

| | | 2a = 5 mm | | 2a = 6 mm | | 2a = 7mm | | 2a = 8 mm | |
|---|---|---|---|---|---|---|---|---|---|
| ΔF (dpt) | $R_1$ (mm) | Δh (μm) | ΔV (μl) | Δh (μm) | ΔV (μl) | Δh (μm) | ΔV (μl) | Δh (μm) | ΔV (μl) |
| 0 | 7.53 | 0 | 0 | 0 | 0 | 0 | 0 | 0 | 0 |
| 1 | 9.09 | 76.3 | 0.8 | 113.7 | 1.7 | 161.5 | 3.2631 | 222.2 | 5.5 |

TABLE 1-continued

| | | 2a = 5 mm | | 2a = 6 mm | | 2a = 7mm | | 2a = 8 mm | |
|---|---|---|---|---|---|---|---|---|---|
| ΔF (dpt) | $R_1$ (mm) | Δh (μm) | ΔV (μl) | Δh (μm) | ΔV (μl) | Δh (μm) | ΔV (μl) | Δh (μm) | ΔV (μl) |
| 2 | 11.63 | 155.0 | 1.6 | 229.5 | 3.3 | 323.2 | 6.4733 | 440.1 | 11.7 |
| 3 | 16.20 | 232.9 | 2.3 | 342.9 | 5.0 | 479.8 | 9.5393 | 648.1 | 17.0 |
| 4 | 26.90 | 310.5 | 3.1 | 455.3 | 6.6 | 633.8 | 12.524 | 850.6 | 22.7 |
| 5 | 80.20 | 388.0 | 3.8 | 567.0 | 8.1 | 786.0 | 15.460 | 1,050 | 27.2 |

Desired corrections can be obtained with a central thickness Δh of the corneal implant 100 in the range of about 100-1,000 μm, e.g., from about 100 to about 350 μm for a 5 mm cut, about 100 to 500 μm for a 6 mm cut, to the extent that the cornea is able to stretch and accommodate the implanted material and increase in thickness. The values in Table 1 are calculated under the assumption that the anterior surface of the cornea does not change due to the cut 102 or implanted filler 112.

As shown in Table 2 for a corneal implant with diameters ranging between 2a=5 mm and 2a=8 mm and an anterior corneal thickness ΔC of 100 μm, the refractive change of the cornea desired can be obtained by a corresponding lifted radius from $R_2$=7.71 mm to $R_2$, the top of the implant, by changing the volume of the cornea ΔV due to the added filler 112. An uncorrected eye with no corneal implant 100 that has no change in focal power ΔF and no added corneal volume ΔV due to the added filler 112 has a radius of curvature $R_2$ of approximately 7.71 mm. A change of 1 dpt in focal power can be obtained with an adjusted radius of curvature $R_2$ of 7.54 mm that corresponds to an added corneal volume ΔV of approximately 230 nl for an diameter of 2a=6 mm, for example. A correction of 8 dpts (the upper range typically required for patients) correlates to a new $R_2$ of 6.49 mm and ΔV of 1,900 nl for a corneal diameter of 2a=6 mm.

TABLE 2

| | | 2a = 5 mm | | 2a = 6 mm | | 2a = 7 mm | | 2a = 8 mm | |
|---|---|---|---|---|---|---|---|---|---|
| ΔF (dpt) | $R_2$ (mm) | Δh (μm) | ΔV (nl) | Δh (μm) | ΔV (nl) | Δh (μm) | ΔV (nl) | Δh (μm) | ΔV (nl) |
| 0 | 7.71 | 0 | 0 | 0 | 0 | 0 | 0 | 0 | 0 |
| 1 | 7.54 | 10.4 | 105 | 15.6 | 230 | 22.2 | 477 | 30.9 | 840 |
| 2 | 7.37 | 20.8 | 211 | 31.3 | 461 | 44.8 | 962 | 62.5 | 1,700 |
| 3 | 7.20 | 31.3 | 317 | 47.1 | 695 | 67.6 | 1,453 | 94.4 | 2,573 |
| 4 | 7.05 | 41.9 | 424 | 63.0 | 931 | 90.6 | 1,951 | 127 | 3,465 |
| 5 | 6.90 | 52.5 | 531 | 79.0 | 1,170 | 114 | 2,454 | 160 | 4,372 |
| 6 | 6.76 | 63.1 | 640 | 95.2 | 1,410 | 137 | 2,966 | 193 | 5,300 |
| 7 | 6.62 | 73.9 | 749 | 112 | 1,654 | 161 | 3,485 | 227 | 6,248 |
| 8 | 6.49 | 84.6 | 859 | 128 | 1,900 | 185 | 4,013 | 262 | 7,218 |

Desired corrections can be obtained with a central thickness Δh of the corneal implant 100 in the range of about 10-260 μm. The values in Table 2 are calculated under the assumption that the posterior surface of the cornea does not change due to the cut 102 or implanted filler 112.

Refractive Changes Due to Corneal Implants

The values listed in Tables 1 and 2 above are calculated under the assumption that the filler volume ΔV does not change after injection. It might be that depending on the filler material, volume changes after implantation occur, e.g., due to the exchange of free water, requiring adaptation of the values in Tables 1 and 2.

As disclosed herein, total corneal refraction consists of two refractive parts, the anterior refraction (between the air and superior or anterior corneal surface) and the posterior part (between the posterior or inner corneal surface and the anterior chamber fluid surface). If the filler material is injected into a deep cut, the posterior surface flattens, which leads to an increased refractive power of the cornea. A similar increase in refractive power also occurs when a superficial cut is made and filled with filler material. Therefore, both refractive changes need to be taken into account.

In some embodiments, corneal correction can include adjustments due to both of these refractive changes applied in series. For example, a deep cut 103a in the bottom portion of the cornea can be made and injected to flatten the posterior portion of the cornea, resulting in a significant change in overall corneal power. A second, superficial cut 103b in the top portion of the cornea can be made (either immediately, or after some passage of time) and injected to bulge the anterior surface of the cornea, resulting in an additional significant change in the overall corneal power. A first injection of filler material resulting in a first implant 100a and a second injection of material resulting in a second implant 100b is shown in FIG. 5B. These two injections result in a top part of the cornea 14a above the second implanted filler material 112a, a bottom part of the cornea 15b below the first implanted filler material 112b, and a central part of the cornea 14c between the deep and superficial cuts and implants 100a, 100b. The deep cut can be used to fine-tune or correct to the precise desired refractive change and/or change in refractive index. Alternatively, this deep cut can be made after some months or years to make a newly needed correction to the already adjusted eye. Also alternatively, the superficial cut can be made before the deep cut.

To ensure that the patient's eye is being adjusted precisely, a first injection can be placed, and the result measured by OCT. If needed, the surgeon can adjust the filler amount of the first injection. Alternatively, the surgeon can create a second, superficial cut and inject the second cut with a second filler amount. The results of the change in the optical behavior of the cornea can be measured by OCT (or other suitable method like the Scheimpflug principle, etc.) before and after each injection, allowing the surgeon to fine-tune the result.

Moreover, the values listed in Tables 1 and 2 above assume no change in refractive index between the corneal implant 100 and the cornea 14, Table 1 assumes a constant outer radius of curvature of the cornea R and Table 2 assumes a constant inner radius of curvature of the cornea r. However, the refractive index of the filler material affects the refractive correction. When the filler refractive index is higher than that of the cornea (e.g., for a dense silicone oil), the lenticular shape of the filler provides a positive lens within the cornea 14. In this case, the maximum thickness Δh of the corneal implant 100 can be less than for a filler with refractive index equal to that of the cornea 14. Reflection at the boundaries of the implant 100 occurs approximately in proportion to the square of the refractive index difference. If the laser-cut region 102 has a rough surface, a filler with a refractive index that nearly matches that of the cornea 14 minimizes light scattering at the rough interfaces. In some embodiments, the same refractive index of the implant 100 and cornea 14 yields correction due only to shape change and change the radius of curvature of the cornea 14 subsequent to implanting the implant 100. The major effect is changing the outer radius of curvature or inner radius of curvature of the cornea 14, with the implant 100 taking up more space.

In other embodiments, a corneal implant 100 with a refractive material that is different from the cornea 14 can be used. The change in refractive index can be used to add to the correction. In this case, the corneal implant 100 functions like an additional lens. A corneal implant 100 with a different index of refraction can be used to partially correct the focal point F, and can be used in conjunction with the altered geometry of the cornea 14 to achieve the desired correction, particularly if high refractive corrections should be achieved, e.g., in compensating the lens refraction after cataract surgery without implantation of intraocular lenses (IOLs).

Biology and Filler Materials

As shown in FIGS. 1A and 1B, an eye 10 is made of various parts, including the cornea 14, and sclera 22 ("white" of the eye). The cornea 14 is made from embryonic skin, and shares much of the same basic structure, with important differences. Early in development, a patch of skin adheres to the developing eye, separates, and differentiates into the cornea 14 and sclera 22. The sclera 22 is not transparent, contains blood vessels, becomes easily inflamed by various stimuli, and is nearly as thick as skin. The cornea 14 is transparent, about 0.5 mm thick, contains no blood vessels, has a low water content, high collagen content, and very regularly arranged layers of aligned collagen fibers rather than the fibrous pattern of dermal collagen. Endothelial cells at the base of the cornea 14 pump ions and water into the anterior chamber, which keeps the cornea transparent by maintaining its refractive index closer to that of the collagen fibrils.

An important difference between the cornea and skin is that the cornea 14 is "immune privileged," meaning that inflammatory reactions are potently suppressed. The immune privilege arises from several mechanisms, including immunosuppressive signaling factors and the absence of blood vessels that transport lymphocytes and other cells responsible for inflammation. The cornea immune privilege is so strong that corneas can be transplanted from one person to another without matching for immunologic compatibility. Accordingly, a wide range of transparent, non-toxic materials could be implanted in the cornea 14 without provoking an immune response.

Another aspect of corneal immune privilege is quiescence of its keratocyte population. Keratocytes are the connective tissue cells primarily responsible for maintaining the connective tissue matrix, including its response to foreign bodies and injuries. The connective tissue matrix consists largely collagen, elastin and glycosaminoglycans like HA. When the matrix is disturbed in skin, an intense wound repair response occurs that is largely mediated through fibroblast activity, often leading to a scar. By contrast, disturbing the cornea matrix elicits little or no inflammatory response, followed by almost no healing, especially for small precise wounds. Laser cutting can be confidently performed without causing a light-scattering scar and corneal cataract as the precise cutting and tissue removal by a laser elicits little or no response from the remaining cornea.

In the present methods, transparent tissue filler materials, similar to the transparent fillers used in dermatology, are used to change the shape of the cornea, e.g., a hyperopic cornea, and correct vision. Tissue filler materials are widely used in dermatology to replace or supplement volume in soft tissues of the skin, subcutaneous fat and/or underlying fascia layers. These filler materials are injectable materials, which after passing through a needle remain at or near the site of injection rather than dissolving.

Materials that are well suited to use for corneal injection are materials that are flowable through a very small needle, having a viscosity that is low enough to allow the material to flow through a small (e.g., 32 gauge or smaller) needle and to spread completely within the corneal cut. At the same time the filler materials must have a viscosity that is high enough to be stable within the corneal environment and able to withstand forces due to eye pressure, eye movement, blinking, and the rigidity of the cornea itself. For example, the viscosity of the filler can be between 5,000 and 130,000 cP (centipoise), e.g., between 7,300 and 125,000, between 7,300 and 63,000, and between 50,000 and 119,000. Materials with the appropriate viscosity can include non-aqueous fillers, such as silicone, and aqueous fillers such as HA and polyethylene glycol (PEG).

The filler materials must be biologically stable within the cornea, being resistant to enzymatic degradation. The fillers must be biocompatible, non-antigenic (although the cornea is immune privileged, strongly antigenic filler materials should be avoided), non-toxic, and non-irritating. The fillers must at the same time be permeable enough to permit oxygen and nutrient transfer through the filler and cornea. This is because a thin layer of live cornea overlying the filler receives much of its nutrients and eliminates much of its waste products of metabolism, by diffusion of these substances through the underlying filler. When placed close to the endothelial inner surface of cornea, fillers can be less permeable, or even impermeable. Examples such as silicone oils are impermeable to water and small polar molecules such as many proteins and metabolites, which fillers such as crosslinked HA are permeable to water and small polar molecules.

The filler materials must also be transparent so as not to interfere with or reduce light transmission through the cornea, and must not be light scattering. Some of the presently used dermal fillers are transparent, which is important for the methods described herein, but transparency is not necessary to their function as dermatological fillers. In particular, HA and silicone fillers are transparent. Collagen fillers have more or less light scattering, depending on the structure and concentration of collagen used. All of the stimulatory fillers now used in dermatology have substantial light scattering, making them translucent or opaque-white in appearance. These fillers are also designed to stimulate tissue responses, hence the nomenclature of stimulatory fillers. Neither light scattering nor tissue stimulation are desired for corneal fillers. The scattering is caused by refractive index mismatch between the aqueous phase (n=1.34) and solids in the filler (collagen n=1.5; silicone n=1.34-1.58). In dermatology, placement of transparent fillers into the upper dermis cause an undesired blue color due to the Tyndall effect. This is not a problem the invention, since the Tyndall effect requires wavelength-dependent scattering in the surrounding dermis. Because cornea is not strongly light scattering, the Tyndall effect will not occur when transparent filler materials are used in cornea.

Acceptable refractive indices of the filler materials are similar or higher than that of the cornea (n=1.376), for example silicone with n=1.34-1.58. The refractive index of the filler material, as well as the geometrical and volumetric effects referred to above, also affects the refractive power of the eye. Refractive index of the filler material is therefore an important factor in filler material design. The refractive index of many fillers can be tuned by changes in filler composition, e.g. the amount of solid material, crosslinking, and water binding by filler materials can affects refractive index. By using a filler material with a refractive index higher than that of the cornea, an even greater refractive correction can be achieved, e.g., up to about a total of about 30 diopters. For example, for the deep cut, if the refractive index of the filler material is higher than that of the cornea, e.g., about 1.4 to 1.6, e.g., about 1.5, e.g., 1.45 to 1.55, or 1.53 to 1.58 (e.g., if the filler material is a silicone oil or silicone oil gel), and the amount of filler material is sufficient to flatten the interior surface of the cornea, then the lenticular-shaped filler material itself can add an additional refractive change of about 10 to 25 diopters, e.g., about 12 to 23 diopters, 14 to 21 diopters, 15 to 20 diopters, or 16 to 18 diopters, which when added to the change caused by the flattening, provides an overall refractive correction of about 14 to 30 diopters, e.g., 16 to 28 diopters, 18 to 26 diopters, 20 to 24 diopters.

In addition, water exchange will take place between the corneal implant 100 and the surrounding cornea after implantation, proportional to the amount of free water (vs. bound water) in the implant that is available for exchange. The amount of bound water in the cornea is very small, making up less than 10% of the total corneal water, and so nearly all water is available for diffusion and possible interaction with the free water in the implant. A stable filler material must have free water activity similar to that of cornea water. Alternatively, the implant can have minimal free water and/or be hydrophobic material with low water content, so as to reduce water exchange with the cornea, e.g., less than 10%, less than 5%, less than 1%.

In some embodiments, overcorrection can be applied to the amount of injected material. This overcorrection can include a greater amount of filler material to be injected than as shown in e.g., Tables 1 and 2. The excess filler material can account for the interaction of the free water in the filler and cornea. The surgeon can monitor and correct these changes due to free water content in the hours following injection, or in a subsequent patient visit. This overcorrection can also account for any leakage or other discrepancies between the theoretical, injected amount and subsequent measurements (e.g., as shown in Examples 1 and 2 below).

The filler materials can be liquids or gels, e.g., hydrogels, and can be derived from natural components. For example, the filler materials can be derived from tissue components such as collagen and/or hyaluronic acid, crosslinked polysaccharides, natural proteins or protein gels, agars, etc., or can be composed of manmade materials such as silicone oil, silicone gel, perfluorocarbons or perfluorocarbon polymers, synthetic protein gels, synthetic polysaccharide, polyethylene glycols, flowable polymer or polymers. Perfluorocarbons have been used occasionally in the eye support to support or replace the vitreous humor. Other natural or man-made materials now used in some dermal fillers are not appropriate for use as described herein. These include hydroxyapatite, a solid light-scattering component of bone, any solid particle larger than about 50 μm diameter that inhibits injection through needles, and any material that is unstable, toxic or irritating to cornea. Small particles made of transparent biocompatible material such as polymethylmethacrylate, other plastics, glass, fused silica, etc., can be suspended in the cornea filler provided that the suspension is flowable, and that the suspension has little or no optical turbidity. Turbidity is due to optical scattering. If the refractive index of particles exactly matches that of the flowable liquid in which they are suspended, there is no optical scattering. For particles that are not exactly matched to the flowable liquid in which they are suspended, the size, shape, and number of particles determines optical scattering. Optical scattering if present in the filler, produces a visual haze effect that becomes stronger with the amount of scattered light.

Of these dermatological fillers, some stimulate a tissue response, e.g., an immune response, while others stimulate little or no tissue response. Stimulatory PMMA and hydroxyapatite fillers such as Bellafill® and Sculptra® cause a prolonged phase of inflammatory response, new connective tissue growth, granulomas, and/or new blood vessel formation.

In contrast, non-stimulatory, e.g., non-immunostimulatory, fillers are designed to mimic normal tissue, producing little or no inflammatory reaction when the material is introduced. The most common non-immunostimulatory fillers are composed largely or entirely of cross-linked hyaluronic acid (HA) in a gel or dense aqueous solution such as Restylane®, and/or of human or bovine type I collagen in various forms. Collagen and HA are major constituents of normal connective tissues, including skin and cornea 14. These fillers are long lasting, but because they are susceptible to natural tissue turnover, are eventually degraded by enzyme action over time. Some of the collagen fillers as used in dermatology are optically scattering and would not be appropriate as a corneal filler.

Crosslinking is used to retard the filler loss due to chemical and enzymatic degradation, and the type of crosslinking used can greatly extend the useful effect of non-immunostimulatory fillers. For example, Restylane® HA filler typically lasts about 3 months after skin injection, whereas Evolence®, an HA filler crosslinked with ribose, lasts about 12 months after skin injection. The proven one year stability of ribose-crosslinked HA in skin is will translate into stability for a decade or more in cornea due to its immune privilege. HA gel such as Juvederm® dermal filler can be used, which has a viscosity ranging between 7,300 and approximately 63,000 cP (centipoise) depending on the specific formulation. Perlane® HA fillers, which are part of the Restylane® family can also be used, with Perlane® having a viscosity of approximately 125,000 cP and Restylane having a cP of approximately 119,000 cP.

Any filler material injected into immune privileged cornea would last considerably longer than in skin.

Other materials of great interest are pure silicone oils, or silicone gels. Silicone was previously used as a dermal filler with initial problems, because the material used was contaminated with other substances that caused inflammatory tissue reactions. When highly purified silicone is used, there is essentially no tissue reaction in skin, which implies even less tissue reaction in cornea. Silicone has the advantages of being very inert and hydrophobic, such that the lenticular-shaped implant of silicone as described herein will be highly stable. Silicone derivatives that can be crosslinked are also available, and have been used for years as elastomers and adhesives in medical device implants.

While in different embodiments all the filler materials described herein can be used, the preferred embodiments use non-immunostimulatory fillers that are transparent, long-lasting, have a known and largely uniform refractive index, and are stable mechanically, chemically and biologically. These requirements can be fulfilled with crosslinked HA, dilute collagen fibrils, collagen gel, and/or silicone-based or other formulations, including mixtures of these components, within the range known to be safe and well tolerated in the other human uses of fillers.

Also suitable are fillers that become highly viscous and/or are crosslinked upon exposure to the low water content of the cornea, and/or fillers that can be crosslinked by addition of a crosslinking agent, e.g., a photo-crosslinking agent such as rose Bengal, riboflavin, pthalocyanines, and the like, which can be activated by specific wavelengths of light. Of these, rose Bengal and riboflavin are particularly well suited, because of a history of safe use in the eye using green light or near-ultraviolet radiation, respectively, in humans.

Ribose-crosslinked HA fillers are particularly suited for use as filler material 110 for a corneal implant 100. These fillers are crystal clear, have a refractive index nearly matching that of cornea, are easily flowable, but become highly viscous upon water exchange to form a dense free filler. They can be photo-crosslinked to create a fixed filler that can also be adherent to the cornea tissue to create a bonded filler. Furthermore, since this material can be rapidly hydrolyzed by hyaluronidase, future corrections could be carried out without the need to make another intra-cornea laser cut.

For application as a corneal filler, some permeability of the filler material 110 is crucial. To maintain health, the cornea 14 requires oxygen, nutrients and waste products to be transported by diffusion from or to the outer and inner part of eye. Without this transport, the outer part of the cornea can lose function and cohesion. To ensure this transport, permeability above a minimum threshold is necessary to keep the cornea supplied with e.g., oxygen and nutrients. The final corneal implant 100 should therefore have permeability that ensures sufficient transport. Transport by diffusion follows Fick's Law, which states that the flux of material transported is proportional to a diffusion constant D of the material in the corneal filler layer, proportional also to the concentration gradient across the layer, and inversely proportional to the layer thickness. In general, materials that are permeable to oxygen, water, glucose, and other small metabolite molecules are appropriate.

The filler material 110 composition can be one of the aqueous formulations such as HA or PEG, where water will be exchanged between the filler and the cornea tissue. Water exchange happens rapidly, typically within tens of minutes. Because water content of the cornea 14 is tightly regulated by its endothelium, a highly reliable equilibrium is reached that influences the final water content and volume of the aqueous filler. Typically, higher water content allows aqueous fillers to flow more easily, because their viscosity is inversely related to water content. This property, and the exchange of water between filler and cornea, is advantageously applied. An aqueous filler can be formulated to flow easily during injection, which upon water loss to the cornea after injection, becomes viscous and/or forms a gel.

Water in both collagen and HA fillers, is either "free" (flowable) or "bound" (adherent to the protein or glycosaminoglycan molecules). As the free water is removed from aqueous fillers, the bulk material property of viscosity increases. When sufficient free water is removed, adjacent macromolecules of the filler can adhere to each other, creating a non-flowable gel. Composition and water content of the transparent filler can be adjusted such that the final shape and volume $\Delta V$ of the added filler material 112 are stable within the cornea. Removal of water from a filler material can also affect its refractive index.

In some embodiments, after equilibration with the cornea the added filler material 112 is still flowable, a "free filler." In other embodiments, the filler material is not flowable after equilibration with the cornea, giving a "fixed filler" embodiment. If the fixed filler is furthermore attached to the surrounding cornea, the corneal implant 100 is a "bonded filler."

All three embodiments are useful corrections for hyperopia, with various advantages. Refractive correction of a free filler can be easily adjusted if necessary, by simply adding or removing a small amount of filler substance via syringe 160. The fixed filler is mechanically more stable, while the bonded filler is very mechanically stable and able to maintain an arbitrary shape. Fixed and/or bonded fillers cannot be easily extracted from the cornea 14, because the filler material is no longer flowable. However, this situation can be overcome if the fixed or bonded filler must be removed, by incorporating HA as a major component of the filler. HA, even after extensive crosslinking, is rapidly hydrolyzed by the natural enzyme, hyaluronidase. An injectable solution of bovine or human hyaluronidase is used in ophthalmology during vitrectomy procedures, and is routinely used "off label" in dermatology for removal of unwanted HA fillers. Typically, HA fillers are dissolved within minutes following exposure to hyaluronidase, which is commercially available for human use, e.g. as Vitrase®.

Further embodiments relating to the corneal implant 100 involves crosslinking the added filler material 112, allowing the final shape of the cornea-air interface which accounts for light refraction to be finely tuned. Photo-crosslinking typically requires a light-absorbing activator to be included in the formulation of the filler material 110. Rose Bengal at concentrations up to about 1% can be added, then later exposed to green or yellow light for the photo-crosslinking step. Rose Bengal has been applied to human corneas for decades, as a diagnostic aid to find corneal abrasions. Photo-crosslinking by Rose Bengal of cornea 14 and of collagen solutions has been described in detail. Riboflavin is a naturally occurring compound that absorbs near-infrared light. It is used after topical application to produce photo-crosslinking of cornea as a treatment for keratoconus.

After injection of a desired volume $\Delta V$ of added filler 112, a contact lens 170 that holds the cornea surface into the desired shape for a given refractive correction can be applied. With the cornea 14 held in a preferred surface curvature and shape, the added filler material 112 underlying the cornea surface can be actively crosslinked such that it becomes much more solid, becomes attached to the surrounding cornea, and thus maintains the desired cornea surface shape. Photo-crosslinking is a means of achieving this version of a fixed or bonded filler. The contact lens 170 used can be transparent to allow photo-crosslinking of the filler while holding the cornea in the desired shape. The contact lens 170 can be discarded once the desired shape of the cornea 14 is achieved.

The degree of crosslinking can be controlled using known techniques to control the degree of crosslinking of the in-place corneal implant 100. A more highly crosslinked corneal implant 100 has a higher refractive index and is more stable and durable. A surgeon could make fine corrections to the eye 10 by a finely changing the level or amount of crosslinking.

In some embodiments, crosslinking can be used to control the viscosity of the corneal implant before the filler material is injection into the cornea.

In some embodiments, the corneal implant is fixed in place within the corneal cut, e.g., by a tissue adhesive or by crosslinking components of the filler material to elements of the corneal tissue at the interface between the surface of the corneal implant and the internal surface of the corneal cut. For example, a non-toxic crosslinking agent that is mixed into the filler material and used to solidify the corneal implant can also be used to simultaneously cause components at the surface of the corneal implant to bind to elements of corneal tissue lining the corneal cut. Fixing the implant in place is particularly advantageous as blinking creates mechanical forces on the cornea that tend to displace the implant.

In other embodiments, either a tissue adhesive (such as fibrin, fibrinogen, or fibronectin) or a non-toxic crosslinking agent (as described herein) can be injected into the interface between the corneal implant and the corneal cut after the corneal implant has been solidified. The tissue adhesive can then be allowed to cure or the crosslinking agent can be activated to cause components of the filler material to become crosslinked to elements of the corneal tissue.

Alternatively (or in addition), the corneal implant can be fixed in place by applying a crosslinking agent, e.g., a photo-crosslinking agent such as Rose Bengal, riboflavin, or Methylene Blue, to an internal surface of the corneal cut before the filler material is injected into the corneal cut. Thereafter, one can wait for a time sufficient for water in which the crosslinking agent (e.g., Rose Bengal) is administered to pass out of the space in the corneal cut, which leaves the Rose Bengal behind, bound to the internal surfaces of the corneal cut. Excess crosslinking agent solution can also be simply withdrawn from the space in the corneal cut, e.g., with a syringe. Thereafter, the filler material can be injected and solidify as noted herein. Once the corneal implant is solidified, the crosslinking agent can be activated to crosslink components of the corneal implant with elements of the corneal tissue lining the internal surfaces of the corneal cut. For example, Rose Bengal, is activated with green or yellow light.

In some embodiments, the corneal implant can be crosslinked from the outer surface, e.g., using a crosslinking agent that is applied to the inner surfaces of the corneal cut, so that the corneal implant is partially solidified on the outside surface, but retains a central core that is a semi-solid or liquid. This configuration permits a doctor to more easily change the level of visual correction by removing from or adding to the corneal implant by withdrawing some of the liquid filler material or adding additional liquid filler material to the corneal implant with a fine syringe. Once the final desired correction is achieved, the entire corneal implant can be solidified, or the central liquid core can be maintained, e.g., in younger patients whose vision could change over time.

Certain filler materials have been described that are known in the medical field, including crosslinked HA, dilute collagen fibrils, collagen gel, and/or silicone based formulations, and mixtures of these components. However, other non-stimulatory fillers that are transparent, long-lasting, with a uniform refractive index, and are stable mechanically, chemically and biologically could be developed.

Implant Geometry

Figure 7A:
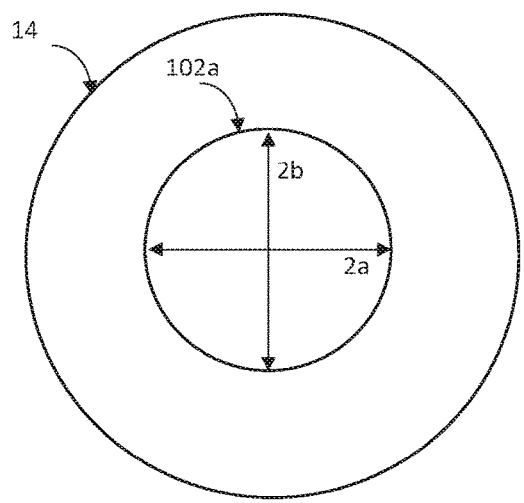
FIGS. 7A-7D are top schematic views of a cornea implanted with various corneal implants.
Figure 7B:
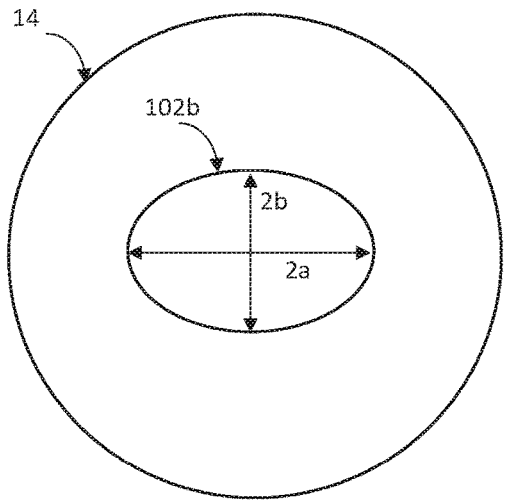
Figure 7C:
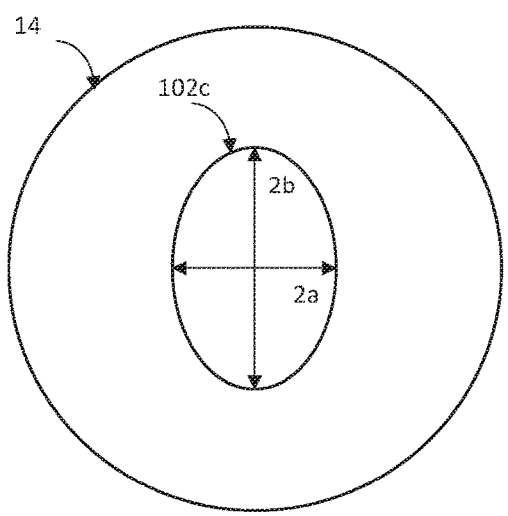
Figure 7D:
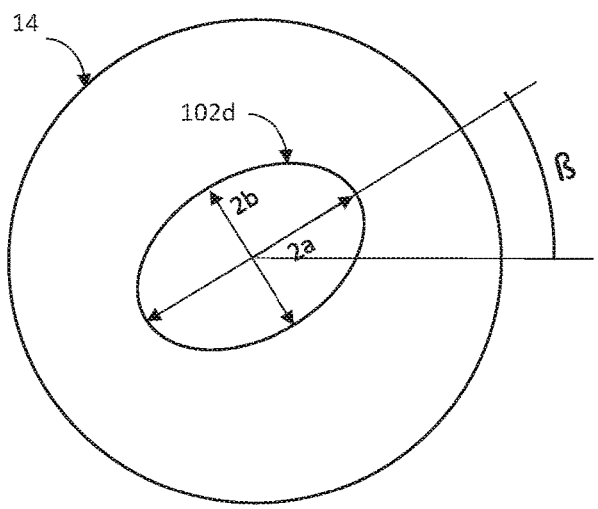

As shown in FIGS. 7A-7D, the methods described herein can be adapted for correction of hyperopia and/or astigmatism. FIG. 7A shows a top view of the cornea 14 with the circular cut 102a. The circular cut 102a, and the subsequent shape of the corneal implant 100 are circular and symmetric, located at the central optical axis 24 of the cornea 14, and uniformly refracts light incident on the cornea 14 at all angles. If astigmatism is also to be corrected, the shape of the laser cutting can be made ovoid rather than circular, with one axis of the cut and subsequent shape longer than the other, as shown in FIGS. 7B and 7C. In such embodiments, the long axis of the oval can be oriented across the axis of astigmatism, with a horizontal cut 102b and axis $2a>2b$ (FIG. 7B), a vertical cut 102c with axis $2a<2b$ (FIG. 7C), or at any angle $\beta$, matching the axis of the astigmatism $\beta+-90$ degrees (FIG. 7D). Thus, both astigmatism and hyperopia can be simultaneously corrected.

Quantification of spherical and astigmatic correction and their relation between the two axis a and b, the volume $\Delta V$ and the refractive correction is more complicated than in the symmetric case of FIG. 7A for the spherical correction. Several assumptions about the three dimensional ellipsoidal shape of the implant have to be made before an analytical or numerical integration of the implant volume $\Delta V$ leads to precise relation between the spherical and astigmatic optical correction and the parameters a, b and $\Delta V$.

In some embodiments, one could take advantage of the photo-crosslinking of the filler material. One could inject the filler, and after stabilization perform diagnostic tests to ensure the appropriate correction level had been obtained. When desired one could then photo-crosslink the implant, freezing it in shape and in place.

One could also take advantage of the reversibility of crosslinking of the various materials described herein. For example, in the case of HA, hyaluronidase is known to catalyze the hydrolysis of HA, by lowering its viscosity and increasing its permeability. Application of hyaluronidase would effectively de-crosslink the in-place corneal implant 100. In cases where a change to the existing implant is necessary, such as surgical error, or changes to the eye or any deterioration of the implant over time, one could apply hyaluronidase to de-crosslink the filler material. The surgeon could then replace the implant, reshape the implant, or remove the implant by aspiration, as desired.

EXAMPLES

The invention is further described in the following examples, which do not limit the scope of the invention described in the claims.

Example 1—Deep Corneal Filler Test

Figure 8A:
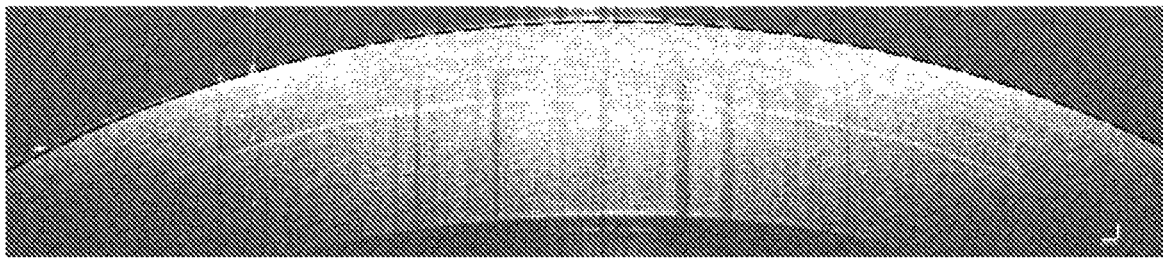
FIGS. 8A-8C are Optical Coherence Tomography (OCT) scans taken before and after corneal implants of two sizes were inserted into deep corneal cuts.
Figure 8B:
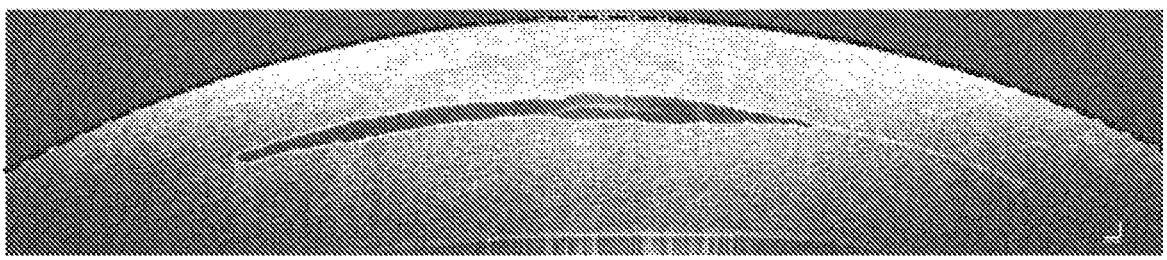
Figure 8C:
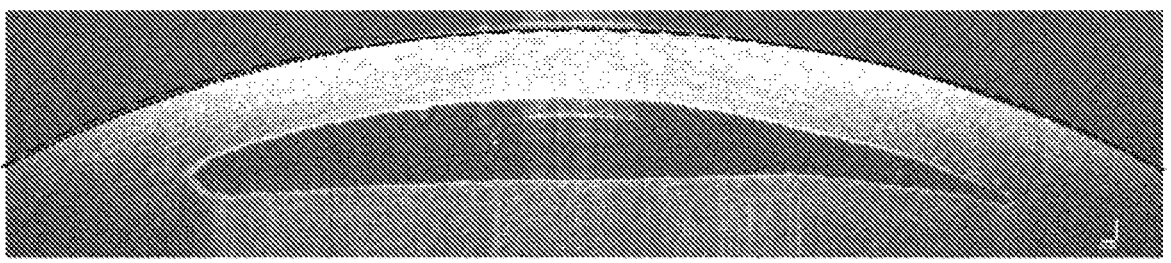
Figure 9A:
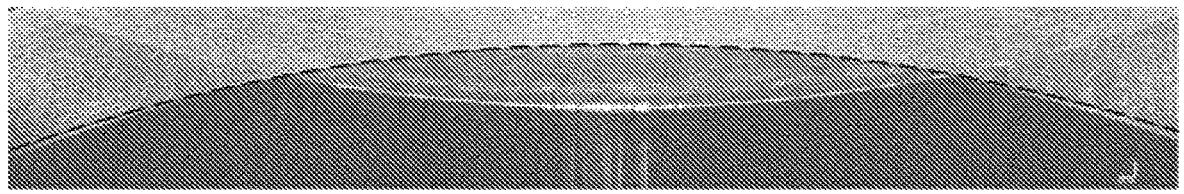
FIGS. 9A-9C are OCT scans showing radii of curvature before and after corneal implants were inserted into deep corneal cuts.
Figure 9B:
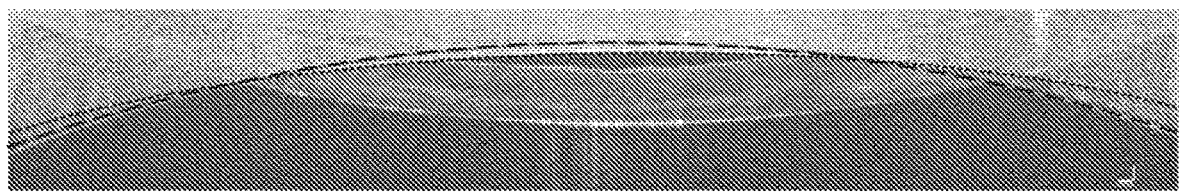
Figure 9C:
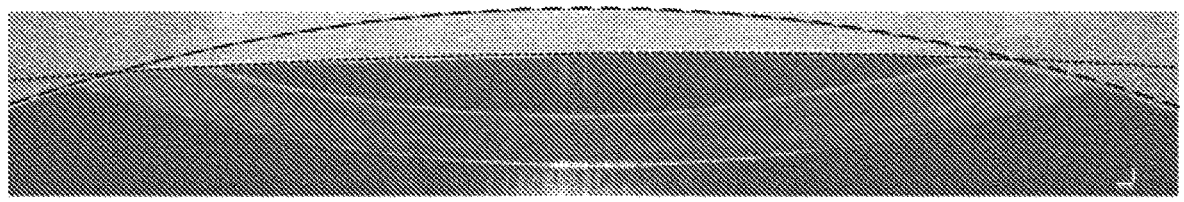

An experiment was carried out to test the efficacy of a corneal filler implanted into a deep corneal cut. A freshly enucleated pig eye was pressurized with a water column to an intraocular pressure of 20 mmHg. The cornea of a pig eye is roughing 1 cm thick, approximately double the thickness of a human cornea. A cut of 5 mm diameter and 500 μm deep was scanned with a 355 nm, 400 ps laser and a pulse energy of 1 μJ, using a 2 μm×2 μm spot separation. The cut was injected sequentially with 1.5 μl and then 6 μl of J. Ultra Plus XC filler material. As shown in FIGS. 8A-8C, Optical Coherence Tomography (OCT) scans were taken before the first filler injection and after each filler injection. FIGS. 9A-9C indicate radial surface fits at the same time points.

Table 3 shows the resulting changes in corneal optical and physical properties at these time points. A refraction change of 1.1 dpt and 3.3 dpt can be achieved with a filler volume of 1.5 μl and 6 μl respectively in a 5 mm diameter filler size. The results are comparable with the calculations for a standardized human eye, where an injection of 0.77 μl and 2.3 μl leads to 1 dpt and 3 dpt refraction change respectively. The difference between the injected (1.5 μl and 6 μl) and the measured (0.97 μl and 3.6 μl) volume were due to inhomogeneous filler distribution in the pocket and leakage of filler material during the injection process. The difference between calculated filler amount and resulting injected volume can be tabulated and used to overcorrect the need amount of filler volume to inject during a treatment.

TABLE 3

| Injection | R (mm) | F (dpt) | R (mm) | F (dpt) | Ftot (dpt) | ΔF (dpt) | Δh | ΔV (μl) |
|---|---|---|---|---|---|---|---|---|
| before | 8.27 | 45.5 | 11.6 | −3.5 | 42.1 | — | — | — |
| after 1.5 μl | 8.23 | 45.7 | 15.9 | −2.5 | 43.2 | 1.1 | 100 | 0.97 |
| after 6 μl | 8.14 | 46.2 | 52.2 | 0.79 | 45.4 | 3.3 | 500 | 3.6 |

The results show that deep cuts and filler injection can successfully modulate the posterior surface, leading to a decrease (flattening) of the curvature with a fine-tunable decrease of the negative refractive power (also an increase of optical power) of that surface up to about 5 dpt.

Example 2—Superficial Corneal Filler Test

Figure 10A:
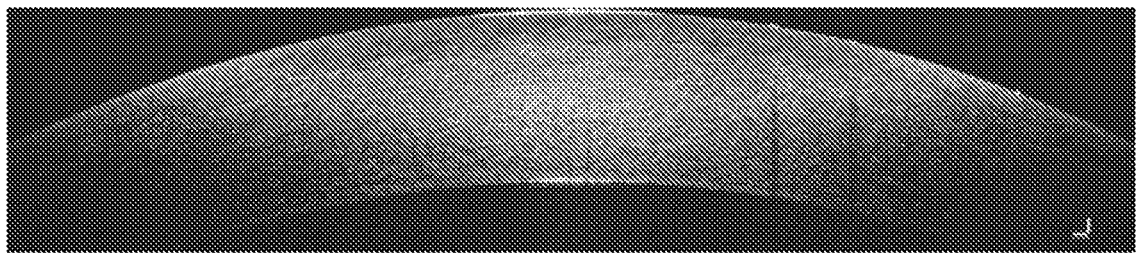
FIGS. 10A-10C are OCT scans taken before making a superficial cut into a cornea, after making the superficial cut, and after the corneal implant was inserted into the superficial corneal cut.
Figure 10B:
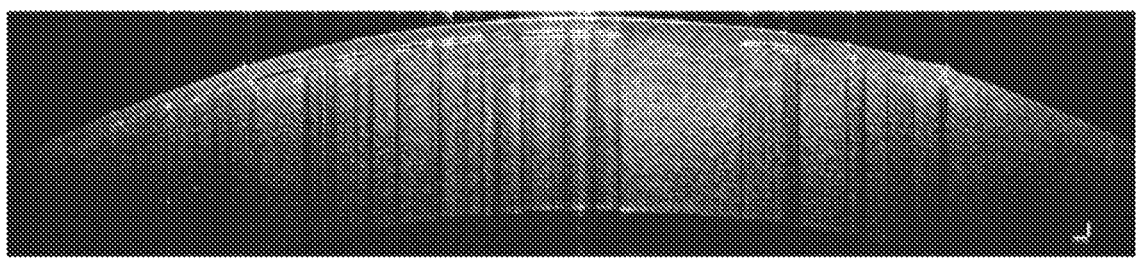
Figure 10C:
Figure 11A:
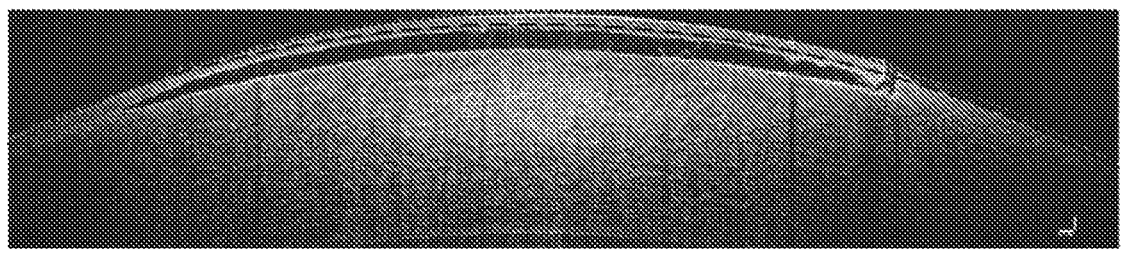
FIGS. 11A-11B are OCT scans showing radii of curvature before (dashed line) and after the corneal implant was inserted into the superficial corneal cut.
Figure 11B:
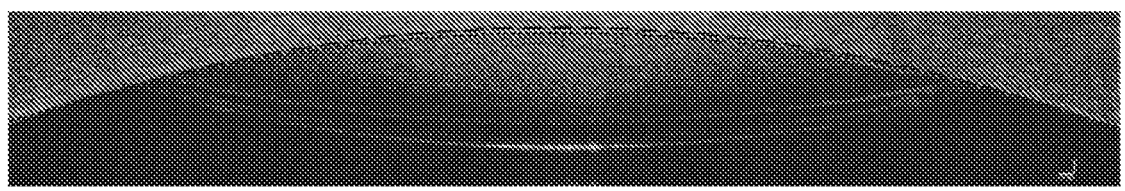

An experiment was carried out to test the efficacy of a corneal filler when implanted into a superficial corneal cut. A freshly enucleated pig eye was pressurized with a water column to an intraocular pressure of 20 mmHg. A cut of 6 mm diameter and 100 μm deep was scanned with a 355 nm, 400 ps laser and a pulse energy of 690 nJ, using a 2 μm×2 μm spot separation. The cut was injected with 2 μl of J. Ultra Plus XC filler material. As shown in FIGS. 10A-10C, OCT scans were taken before cutting, after cutting, and after filler injection. FIGS. 11A-11B show radial surface fits of the front and back surfaces after injection.

Table 4 shows the resulting changes in corneal optical and physical properties before and after injection. A refraction change of 5 dpt can be achieved with a filler volume of 1.5 μl in a 6 mm diameter filler size. The results are comparable with the calculations for a standardized human eye, where an injection of 1.17 μl leads to 5 dpt refraction change. The difference between the injected (2 μl) and the measured (1.5 μl) volume was due to leakage of filler material during the injection process.

TABLE 4

| Injection | R (mm) | F (dpt) | R (mm) | F (dpt) | Ftot (dpt) | ΔF (dpt) | Δh (μm) | ΔV (μl) |
|---|---|---|---|---|---|---|---|---|
| before | 8.76 | 42.9 | 11.0 | −3.8 | 39.1 | — | — | — |
| after 2 μl | 7.92 | 47.4 | 11.8 | −3.3 | 44.1 | 5.0 | 100 | 1.46 |

The results show that superficial cuts and filler injections lead to an increase (steepening) of the anterior curvature (decrease of radius) with an effective increase in refractive power.

By varying the depth of the corneal cut to be deep or superficial it is possible to either steepen the outer surface or flatten the inner corneal surface, or do both if a cut is made in the both the superficial an deep layer, resulting in a fine-tunable, precise increase in refractive power of the cornea.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating hyperopia or presbyopia in a patient, the method comprising:
    making a cut deep in the patient's cornea with a pulsed laser to create a two-dimensional (2D) slit adjacent to and generally parallel to a posterior surface of the cornea; and
    injecting a liquid or semi-solid transparent filler material into the deep cut in an amount sufficient to flatten the posterior surface of the cornea to increase the refractive power of the cornea by a predetermined correction of up to about 5 diopters due to the physical flattening of the posterior surface of the cornea, wherein the transparent filler material comprises a refractive index of about 1.3 to about 1.6, and forms a corneal implant with a lenticular shape within the cornea,
    wherein cutting the cornea comprises cutting a two-dimensional (2D) slit centered on an optical axis of the cornea,
    wherein the deep cut is made at a depth of greater than 300 microns from an anterior surface of the cornea,
    wherein the step of making the deep cut does not require making an incision through the corneal surface, and does not require creating a corneal flap.

2. The method of claim 1, wherein the deep cut is made at a depth of greater than 400 microns from an anterior surface of the cornea.

3. The method of claim 1, wherein the transparent filler material comprises a liquid filler material.

4. The method of claim 1, wherein the transparent filler material is not cured or crosslinked so that it maintains a liquid consistency.

5. The method of claim 1, wherein the transparent filler material comprises a hydrogel filler material.

6. The method of claim 1, wherein the filler material comprises a refractive index greater than about 1.4 and causes an additional increase in the refractive power of the cornea due to the lenticular-shaped filler material itself of about 10 to 25 diopters.

7. The method of claim 1, further comprising making a second, superficial cut in the patient's cornea to create a two-dimensional slit adjacent to and generally parallel to the posterior surface of the cornea, and injecting a liquid or semi-solid transparent filler material into the superficial cut in an amount sufficient to increase the curvature of an anterior surface of the cornea to increase the refractive power of the cornea by a predetermined correction of up to about 12.0 diopters due to the physical increased curvature of the anterior surface of the cornea, wherein the transparent filler material forms a corneal implant with a lenticular shape.

8. The method of claim 7, wherein the filler material comprises a refractive index greater than about 1.4 and causes an additional increase in the refractive power of the cornea due to the lenticular-shaped filler material itself of about 10 to 25 diopters.

9. The method of claim 1, wherein the slit is a circularly shaped 2D slit to correct spherical hyperopia.

10. The method of claim 1, wherein the slit is a non-circularly oval shaped 2D slit to correct hyperopic astigmatism.

11. The method of claim 1, further comprising solidifying the filler material after injecting the filler material to form a solid or semi-solid corneal implant.

12. The method of claim 11, wherein solidifying the filler comprises crosslinking the filler.

13. The method of claim 1, wherein the corneal implant has a refractive index of about 1.3 to 1.5.

14. The method of claim 1, wherein the filler material comprises one or more of crosslinked hyaluronic acid (HA), dilute collagen fibrils, collagen gel, and silicone.

15. The method of claim 14, wherein the filler material comprises ribose-crosslinked HA.

16. The method of claim 1, further comprising fixing the corneal implant in place within the corneal cut.

17. The method of claim 16, wherein the corneal implant is fixed in place by crosslinking components of the filler material to corneal tissue or by applying a crosslinking agent to an internal surface of the corneal cut.

\* \* \* \* \*